(12) United States Patent
Tang

(10) Patent No.: US 9,589,099 B2
(45) Date of Patent: Mar. 7, 2017

(54) DETERMINATION OF GENE EXPRESSION LEVELS OF A CELL TYPE

(75) Inventor: Leung Sang Nelson Tang, Kowloon (HK)

(73) Assignee: The Chinese University of Hong Kong, Shatin (CN)

( * ) Notice: Subject to any disclaimer, the term of this patent is extended or adjusted under 35 U.S.C. 154(b) by 322 days.

(21) Appl. No.: 13/555,045

(22) Filed: Jul. 20, 2012

(65) Prior Publication Data

US 2013/0190194 A1    Jul. 25, 2013

Related U.S. Application Data

(60) Provisional application No. 61/510,445, filed on Jul. 21, 2011.

(51) Int. Cl.
| | | |
|---|---|---|
| C12Q 1/68 | (2006.01) | |
| G06F 19/20 | (2011.01) | |
| G06F 19/18 | (2011.01) | |

(52) U.S. Cl.
CPC ........... *G06F 19/20* (2013.01); *C12Q 1/6809* (2013.01); *G06F 19/18* (2013.01)

(58) Field of Classification Search
None
See application file for complete search history.

(56) References Cited

U.S. PATENT DOCUMENTS

| | | |
|---|---|---|
| 6,365,352 B1 | 4/2002 | Yerramilli et al. |
| 7,598,031 B2 | 10/2009 | Liew |
| 7,888,030 B2 | 2/2011 | Butt et al. |
| 2005/0164231 A1* | 7/2005 | Staudt et al. ........... 435/6 |
| 2006/0292572 A1 | 12/2006 | Stuart et al. |
| 2007/0020618 A1 | 1/2007 | Prashar et al. |
| 2007/0037144 A1 | 2/2007 | Wohlgemuth et al. |
| 2007/0070581 A1 | 3/2007 | Yoshida et al. |
| 2011/0070581 A1 | 3/2011 | Gupta et al. |

FOREIGN PATENT DOCUMENTS

| | | |
|---|---|---|
| CN | 1475579 A | 2/2004 |
| CN | 1629315 A | 6/2005 |
| CN | 1629316 A | 6/2005 |
| CN | 101538608 A | 9/2009 |

OTHER PUBLICATIONS

Mihalcik et al. The Journal of Immunology, Jul. 15, 2010, vol. 185 No. 2 1045-1054.*
Koning et al. Journal of Virology 83.18 (2009): 9474-9485.*
Tan et al. Laboratory Investigation (2009) 89, 708-716.*
Mihalcik et al. The Journal of Immunology, Jul. 15, 2010, vol.185; No. 2;1045-1054.*
Fan et al. Clinical Chemistry 55:4;774-785 (2009).*
Shen-Orr et al. Cell type-specific gene expression differences in complex tissues Nature Methods vol. 7, pp. 287-289 and online methods (2010).*
Lossos, I.S., et al., "Optimization of quantitative real-time RT-PCR parameters for the study of lymphoid malignancies," Leukemia, 2003, vol. 17, pp. 789-795.
Koning, F. A., et al., "Defining APOBEC3 expression patterns in human tissues and hematopoietic cell subsets," Journal of Virology, Sep. 2009, vol. 83, No. 18, pp. 9474-9485.
International Search Report and Written Opinion mailed Nov. 15, 2012, PCT/CN2012/079063, 11 pages.
Lu, Peng et al.; "Expression deconvolution: A reinterpretation of DNA microarray data reveals dynamic changes in cell populations"; PNAS; Sep. 2, 2003; pp. 10370-10375; vol. 100, No. 18.
Zhao, Yingdong et al.; "Gene expression deconvolution in clinical samples"; Genome Medicine; 2010; pp. 1-3; 2:93.
Foti, Maria et al.; "Gene Expression Profiling of Dendritic Cells by Microarray"; Methods in Molecular Biology; 2007; pp. 215-224; vol. 380.
Kobayashi, Scott D. et al.; "Genome-Scale Transcript Analyses in Human Neutrophils"; Methods in Molecular Biology; 2007; pp. 441-453; vol. 412.
Pike-Overzet, Karin et al.; "DNA Microarray Studies of Hematopoietic Subpopulations"; Methods in Molecular Biology; 2009; pp. 403-421; vol. 506.
Fan, Hongtao et al.; "The Transcriptome in Blood: Challenges and Solutions for Robust Expression Profiling"; Current Molecular Medicine; 2005; pp. 3-10; vol. 5; No. 1.
Mohr, Steve et al.; "The peripheral-blood transciptome: new insights into disease and risk assessment"; TRENDS in Molecular Medicine; 2007; pp. 422-432; vol. 13; No. 10.
Vartanian, Kristina et al.; "Gene expression profiling of whole blood: Comparison of target preparation methods for accurate and reproducible mircroarray analysis" BMC Genomics; 2009; 10:2; 16 pages.
Weber, Daniel Gilbert et al.; "Assessment of mRNA and microRNA Stabilization in Peripheral Human Blood for Multicenter Studies and Biobanks"; Biomarker Insights; 2010:5; pp. 95-102.
Chaussabel, Damien et al.; "Assessing the human immune system through blood transcriptomes"; BMC Biology; 2010;8:84; 14 pages.
Mesko, Bertalan et al.; "Gene expression profiles in peripheral blood for the diagnosis of autoimmune diseases"; Trends in Molecular Medicine; 2011; pp. 223-233; vol. 17; No. 4.

(Continued)

*Primary Examiner* — John S Brusca
(74) *Attorney, Agent, or Firm* — Kilpatrick Townsend & Stockton LLP

(57) ABSTRACT

Methods, systems, and compositions can determine gene expression level of a specified cell-type subpopulation by direct analysis of a cell mixture sample composed of multiple subpopulations of various cell-types without the need of prior separation of the component cell-type subpopulations. A target gene and a reference gene can be identified as being informative for a specific cell-type subpopulation when at least 50% of the gene's transcripts in the cell mixture are from the subpopulation. This relative expression level in the cell mixture of the informative target and reference genes can correlate to the relative expression when measured in the isolated subpopulation. Thus, a similar biomarker can be obtained without the difficult step of isolating the cells of the subpopulation.

26 Claims, 15 Drawing Sheets

(56) References Cited

OTHER PUBLICATIONS

Laudanski, Krzysztof et al.; "Cell-specific expression and pathway analyses reveal altercations in trauma-related human T cell and monocyte pathways"; 2006; pp. 15564-15569; vol. 103; No. 42, PNAS.
Whitney, Adeline R. et al.; "Individuality and variation in gene expression patterns in human blood"; PNAS; 2003; pp. 1896-1901; vol. 100; No. 4.
Palmer, Chana et al.; "Cell-type specific gene expression profiles of leukocytes in human peripheral blood"; Bmc Genomics; 2006; 7:115; 15 pages.
Watkins, Nicholas A. et al.; "A HaemAtlas: characterizing gene expression in differentiated human blood cells"; 2009; vol. 113; No. 19; 10 pages, Blood.
Bryant, Penelope A. et al.; "Detection of Gene Expression in an Individual Cell Type within a Cell Mixture Using Microarray Analysis"; 2009; pp. 1-10; vol. 4; Issue 2, PLoS One.

* cited by examiner

100

| Hematopoietic Subpopulations in Peripheral Whole Blood sample | Proportion |
|---|---|
| Neurtophils | ~50%-65% |
| Monocytes | ~5% |
| Eosinophils | ~3-5% |
| Lymphocyte subpopulations | |
| -B cells | ~5% |
| -CD4 T cells | ~15-20% |
| -CD8 T cells | ~10% |
| NK cells | ~5% |

| Hematopoietic Subpopulations in Peripheral blood mononuclear cell sample | Proportion |
|---|---|
| Monocytes | ~30% |
| Lymphocyte subpopulations | |
| -B cells | ~10% |
| -CD4 T cells | ~30% |
| -CD8 T cells | ~20% |
| NK cells | ~10% |

FIG. 1B

| 410 | 420 | 430 |
| --- | --- | --- |
| Peripheral Whole Blood | Proportional cell counts (P) of various subpopulations | X50(subpopulation:cell mixture) when the subpopulation contribute 50% of transcript in the cell mixture sample, folds |
| Neurtophils | ~50%-65% | 1 |
| Monocytes | ~5% | 10 |
| Eosinophils | ~3-5% | 10 - 16.7 |
| Lymphocyte subpopulations | | |
| -B cells | ~5% | 10 |
| -total T cells | ~25% | 2 |
| -CD4 T cells | ~15-20% | 2.5 - 3.3 |
| -CD8 T cells | ~10% | 5 |
| -NK cells | ~5% | 10 |

FIG. 4A    400

| 460 | 470 | 480 |
| --- | --- | --- |
| Peripheral blood mononuclear cells | Proportional cell counts (P) of various subpopulations | X50(subpopulation:cell mixture) when the subpopulation contribute 50% of transcript in the cell mixture sample, folds |
| Monocytes | ~30% | 1.7 |
| Lymphocyte subpopulations | | |
| -B cells | ~10% | 5 |
| -total T cells | ~50% | 1 |
| -CD4 T cells | ~30% | 1.7 |
| -CD8 T cells | ~20% | 2.5 |
| -NK cells | ~10% | 5 |

| X, folds | LAF4 | APOBEC3F | DLCAL1 | FREB | KCNG1 | KLHL14 | Prickle | SNX22 | TNFRSF13C |
|---|---|---|---|---|---|---|---|---|---|
| Mean | 6.77 | 2.59 | 32.99 | 36.51 | 15.54 | 9.94 | 11.54 | 6.79 | 9.92 |
| St. Dev. | 3.84 | 1.15 | 22.90 | 19.72 | 12.92 | 5.16 | 7.18 | 3.31 | 5.10 |
| CV% | 56.70% | 44.37% | 69.43% | 54.03% | 83.11% | 51.91% | 62.18% | 48.81% | 51.44% |
| X50 criteria | No | No | Yes | Yes | Yes | Yes* | Yes | No | Yes |
| X80 criteria | No | No | Yes | Yes | No | No | No | No | No |

| ΔΔCT | TNFRSF13C | KLHL14 | FREB | Prickle | DLCAL1 | KCNG1 |
|---|---|---|---|---|---|---|
| Mean | 9.921543 | 9.943549 | 36.51327 | 11.54929 | 32.99363 | 15.54794 |
| St. Dev. | 5.104135 | 5.161469 | 19.72821 | 7.180961 | 22.90609 | 12.9219 |
| CV% | 51.44% | 51.91% | 54.03% | 62.18% | 69.43% | 83.11% |

| X, (folds) of candidate genes | BCL11B | ITK | PRKCQ | CD3G | GIMAP7 | GZMK | LRRN3 | MAF | NELL2 |
|---|---|---|---|---|---|---|---|---|---|
| Mean | 1.88 | 2.16 | 1.61 | 2.23 | 2.34 | 1.84 | 3.20 | 1.72 | 2.72 |
| St. dev. | 1.67 | 1.17 | 0.68 | 0.88 | 1.39 | 0.62 | 1.11 | 0.82 | 1.24 |
| 95% C.I. of mean (upper) | 2.48 | 2.58 | 1.85 | 2.54 | 2.84 | 2.07 | 3.60 | 2.01 | 3.16 |
| X50 criteria | YES | YES | No | YES | YES | YES | YES | YES | YES |

FIG. 10A    1000

| Variance of ddCT in samples of enriched CD3+ve cells collected from 30 individuals | | | | | | | | | |
|---|---|---|---|---|---|---|---|---|---|
| TA by ddCT | BCL11B | ITK | PRKCQ | CD3G | GIMAP7 | GZMK | LRRN3 | MAF | NELL2 |
| Mean | 1.91 | 0.72 | 0.62 | 1.29 | 1.70 | 1.00 | 1.50 | 0.75 | 0.61 |
| St. dev. | 1.14 | 0.22 | 0.21 | 0.37 | 0.33 | 0.37 | 0.49 | 0.31 | 0.23 |
| CV% | 60% | 30% | 34% | 28% | 19% | 37% | 33% | 42% | 37% |

| | Correlation ($R^2$) between Direct LS-TA assays and gene expression in enriched CD3+ T cell samples | | | | | | |
|---|---|---|---|---|---|---|---|
| | BCL11B | ITK | CD3G | GZMK | LRRN3 | MAF | NELL2 |
| Direct LS-TA using GIMAP7 | 0.10 | 0.23 | 0.57 | 0.37 | 0.56 | 0.61 | 0.58 |
| Direct LS-TA using GeoM1 | 0.14 | 0.27 | 0.57 | 0.53 | 0.53 | 0.66 | 0.66 |

| | Comparison of gene expression levels in whole blood and separated granulocytes. | | | | | | | |
|---|---|---|---|---|---|---|---|---|
| X, (folds) of candidate genes | AQP1 | BCL2A1 | CEACAM6 | CEACAM8 | C1orf24 | CSF2 | DEFA4 | FCGR3B |
| Mean | 9.12 | 6.94 | 7.71 | 10.41 | 6.40 | 3.72 | 5.60 | 8.26 |
| St. dev. | 5.82 | 5.32 | 4.18 | 31.84 | 4.44 | 5.33 | 5.47 | 5.76 |
| 95% C.I. of mean (upper) | 10.45 | 8.18 | 8.66 | 17.81 | 7.41 | 5.28 | 6.85 | 9.58 |
| | IL-4 | IL-8 | IL8RB | LTF | MMP25 | MS4A3 | RNASE3 | SOD2 |
| Mean | 61.06 | 26.21 | 7.77 | 3.42 | 10.25 | 1.21 | 5.66 | 6.29 |
| St. dev. | 332.13 | 25.41 | 5.73 | 3.43 | 7.24 | 0.97 | 5.01 | 4.05 |
| 95% C.I. of mean (upper) | 140.59 | 32.64 | 9.08 | 4.23 | 11.90 | 1.44 | 6.80 | 7.22 |

FIG. 12A                    1200

| | Variance of ddCT in samples of separated granulocytes | | | | | | | |
|---|---|---|---|---|---|---|---|---|
| TA by ddCT | AQP1 | BCL2A1 | CEACAM6 | CEACAM8 | C1orf24 | CSF2 | DEFA4 | FCGR3B |
| Mean | 13.03926 | 14.37686 | 7.042252 | 1724.801 | 15.06756 | 4.786464 | 8.149293 | 26.48976 |
| St. dev. | 7.527057 | 13.60841 | 6.676042 | 10676.64 | 11.51594 | 24.63601 | 7.497159 | 24.60146 |
| CV% | 58% | 95% | 95% | 619% | 76% | 515% | 92% | 93% |
| | IL-4 | IL-8 | IL8RB | LTF | MMP25 | MS4A3 | RNASE3 | SOD2 |
| Mean | 281.6566 | 2.259216 | 9.431543 | 3.016567 | 65.83817 | 3.306569 | 22.95174 | 4.601045 |
| St. dev. | 1663.343 | 5.040303 | 8.089712 | 3.991855 | 44.98885 | 2.648231 | 67.79684 | 2.932598 |
| CV% | 591% | 223% | 86% | 132% | 68% | 80% | 295% | 64% |

FIG. 12B                    1250

| Correlation (R2) | BCL2A1 | CEACAM6 | CEACAM8 | C1orf24 | CSF2 | DEFA4 | FCGR3B |
|---|---|---|---|---|---|---|---|
| Direct LS-TA using AQP1 | 0.02 | 0.43 | 0.99 | 0.04 | 1.00 | 0.01 | 0.04 |
| Direct LS-TA using SOD2 | 0.07 | 0.56 | 0.95 | 0.05 | 0.98 | 0.12 | 0.08 |
| | IL-4 | IL-8 | IL8RB | LTF | MMP25 | MS4A3 | RNASE3 |
| Direct LS-TA using AQP1 | 0.13 | 0.85 | 0.11 | 0.40 | 0.03 | 0.18 | 0.57 |
| Direct LS-TA using SOD2 | 0.09 | 0.92 | 0.20 | 0.38 | 0.04 | 0.17 | 0.63 |

FIG. 12C                    1260

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      apolipoprotein B mRNA editing enzyme, catalytic polypeptide-like
      3F (APOBEC3F), transcript variant 1, apolipoprotein B mRNA editing
      enzyme cytidine deaminase

<400> SEQUENCE: 1
aattatgcat tcctgcaccg                                                   20

<210> SEQ ID NO 2
<211> LENGTH: 20
<212> TYPE: DNA
<213> ORGANISM: Artificial Sequence
<220> FEATURE:
<220> FEATURE:
<223> OTHER INFORMATION: synthetic quantitative PCR (QPCR) primer for
      apolipoprotein B mRNA editing enzyme, catalytic polypeptide-like
      3F (APOBEC3F), transcript variant 1, apolipoprotein B mRNA editing
      enzyme cytidine deaminase

<400> SEQUENCE: 2
ccataggctt tgcgtaggtt                                                   20

<210> SEQ ID NO 3
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      dendritic cell-associated lectin-1 (DCAL1), C-type
      lectin-like 1 (CLECL1), transcript variant 1

<400> SEQUENCE: 3
aaaactgttc ggacttcccc                                                   20

<210> SEQ ID NO 4
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      dendritic cell-associated lectin-1 (DCAL1), C-type
      lectin-like 1 (CLECL1), transcript variant 1

<400> SEQUENCE: 4
atgcaccttc cagtctttgg                                                   20

<210> SEQ ID NO 5
```

<211> LENGTH: 20
<212> TYPE: DNA
<213> ORGANISM: Artificial Sequence
<220> FEATURE:
<223> OTHER INFORMATION: synthetic quantitative PCR (QPCR) primer for Fc
receptor homolog expressed in B cells (FREB), Fc receptor-like A
(FCRLA), transcript variant 2, Fc receptor-like and mucin-like 1
(FCRLM1), Fc receptor related protein X (FCRLX, FCRX),
RP11-474I16.5

<400> SEQUENCE: 5
tacctttccc ttggtgtgct                                                20

<210> SEQ ID NO 6
<211> LENGTH: 19
<212> TYPE: DNA
<213> ORGANISM: Artificial Sequence
<220> FEATURE:
<223> OTHER INFORMATION: synthetic quantitative PCR (QPCR) primer for Fc
receptor homolog expressed in B cells (FREB), Fc receptor-like A
(FCRLA), transcript variant 2, Fc receptor-like and mucin-like 1
(FCRLM1), Fc receptor related protein X (FCRLX, FCRX),
RP11-474I16.5

<400> SEQUENCE: 6
cagctgctct cctcagtgc                                                 19

<210> SEQ ID NO 7
<211> LENGTH: 20
<212> TYPE: DNA
<213> ORGANISM: Artificial Sequence
<220> FEATURE:
<223> OTHER INFORMATION: synthetic quantitative PCR (QPCR) primer for
glyceraldehyde-3-phosphate dehydrogenase (GAPDH), transcript
variant 1, universal housekeeping gene internal reference,
aging-associated gene 9 protein

<400> SEQUENCE: 7
caatgacccc ttcattgacc                                                20

<210> SEQ ID NO 8
<211> LENGTH: 20
<212> TYPE: DNA
<213> ORGANISM: Artificial Sequence
<220> FEATURE:
<223> OTHER INFORMATION: synthetic quantitative PCR (QPCR) primer for
glyceraldehyde-3-phosphate dehydrogenase (GAPDH), transcript
variant 1, universal housekeeping gene internal reference,
aging-associated gene 9 protein

<400> SEQUENCE: 8
gacaagcttc ccgttctcag                                                20

<210> SEQ ID NO 9
<211> LENGTH: 19
<212> TYPE: DNA
<213> ORGANISM: Artificial Sequence
<220> FEATURE:
<223> OTHER INFORMATION: synthetic quantitative PCR (QPCR) primer for
potassium voltage-gated channel, subfamily G, member 1 (KCNG1),
potassium channel KH2 (kH2), voltage-gated potassium channel
subunit Kv6.1, potassium channel Kv6.1, K13

<400> SEQUENCE: 9
acctctccgt cagcacctt                                                 19

<210> SEQ ID NO 10
<211> LENGTH: 20
<212> TYPE: DNA

-continued

```
<213> ORGANISM: Artificial Sequence
<220> FEATURE:
<223> OTHER INFORMATION: synthetic quantitative PCR (QPCR) primer for
      potassium voltage-gated channel, subfamily G, member 1 (KCNG1),
      potassium channel KH2 (kH2), voltage-gated potassium channel
      subunit Kv6.1, potassium channel Kv6.1, K13

<400> SEQUENCE: 10
aggaggaact ccagggagaa                                                    20

<210> SEQ ID NO 11
<211> LENGTH: 19
<212> TYPE: DNA
<213> ORGANISM: Artificial Sequence
<220> FEATURE:
<223> OTHER INFORMATION: synthetic quantitative PCR (QPCR) primer for
      kelch-like 14 (Drosophila) (KLHL14), printor,
      protein interactor of torsinA, protein interactor
      of Torsin-1A

<400> SEQUENCE: 11
ctccccagca atttggttc                                                     19

<210> SEQ ID NO 12
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      kelch-like 14 (Drosophila) (KLHL14), printor,
      protein interactor of torsinA, protein interactor
      of Torsin-1A

<400> SEQUENCE: 12
agttttccac ctccacaacg                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      lymphoid nuclear protein related to AF4 (LAF4), lymphoid nuclear
      protein 4, AF4/FMR2 family, member 3 (AFF3), transcript variant 1,
      MLLT2-related protein, MLLT2-like

<400> SEQUENCE: 13
ccaagctctc caagttcagc                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      lymphoid nuclear protein related to AF4 (LAF4), lymphoid nuclear
      protein 4, AF4/FMR2 family, member 3 (AFF3), transcript variant 1,
      MLLT2-related protein, MLLT2-like

<400> SEQUENCE: 14
actttgccag gtgcttgaat                                                    20

<210> SEQ ID NO 15
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      prickle homolog 1 (Drosophila) (PRICKLE1), transcript variant 2,
``` prickle-like 1, REST (RE-1 silencing transcription factor)/NRSF (neuron-restrictive silencer factor)-interacting LIM domain protein (RILP), EPM1B

<400> SEQUENCE: 15
tgcagaactg ctcaaaccac         20

<210> SEQ ID NO 16
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      prickle homolog 1 (Drosophila) (PRICKLE1), transcript variant 2,
      prickle-like 1, REST (RE-1 silencing transcription factor)/NRSF
      (neuron-restrictive silencer factor)-interacting LIM domain
      protein (RILP), EPM1B

<400> SEQUENCE: 16
gtttcacact caaggcagca         20

<210> SEQ ID NO 17
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      sorting nexin 22 (SNX22)

<400> SEQUENCE: 17
gcttggaggc ttacatccag         20

<210> SEQ ID NO 18
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      sorting nexin 22 (SNX22)

<400> SEQUENCE: 18
agttgctagc cttggggtct         20

<210> SEQ ID NO 19
<211> LENGTH: 18
<212> TYPE: DNA
<213> ORGANISM: Artificial Sequence
<220> FEATURE:
<223> OTHER INFORMATION: synthetic quantitative PCR (QPCR) primer for
      tumor necrosis factor receptor superfamily, member 13C
      (TNFRSF13C), B cell-activating factor receptor (BAFF receptor,
      BAFF-R, BAFFR), BLyS receptor 3, prolixin, BROMIX, CD268, CVID4

<400> SEQUENCE: 19
gtgggtctgg tgagctgg         18

<210> SEQ ID NO 20
<211> LENGTH: 20
<212> TYPE: DNA
<213> ORGANISM: Artificial Sequence
<220> FEATURE:
<223> OTHER INFORMATION: synthetic quantitative PCR (QPCR) primer for
      tumor necrosis factor receptor superfamily, member 13C

```
    (TNFRSF13C), B cell-activating factor receptor (BAFF receptor,
    BAFF-R, BAFFR), BLyS receptor 3, prolixin, BROMIX, CD268, CVID4

<400> SEQUENCE: 20
gattcccgga gacagaatga                                                  20
```

DETERMINATION OF GENE EXPRESSION LEVELS OF A CELL TYPE

CROSS-REFERENCES TO RELATED APPLICATION

This application is a non-provisional of and claims the benefit of U.S. Patent Application No. 61/510,445, entitled "METHODS, PROCESS AND COMPOSITIONS FOR DETERMINATION OF GENE EXPRESSION LEVELS OR TRANSCRIPT ABUNDANCE OF A CELL TYPE," filed on Jul. 21, 2011, which is herein incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -94-1.TXT, created on Aug. 29, 2012, 8,192 bytes, machine format IBM-PC, MS-Windows operating system, is hereby incorporated by reference in its entirety for all purposes.

FIELD OF INVENTION

The present disclosure relates to an analysis of gene expression level (transcript abundance) in different hematopoietic subpopulations in blood samples. More particularly, embodiments can determine transcript abundance of a gene in a particular subpopulation of hematopoietic cells in a mixture of different cell types without the need to separate the cells to obtain a cell fraction of the particular subpopulation.

BACKGROUND

Expression levels, transcript abundance (TA), of genes in peripheral blood cells are important biomarkers. Current methods using gene TA in peripheral blood samples as biomarkers are performed in a cell mixture samples of peripheral blood in such a way that no information can be obtained about the TA of a specific hematopoietic subpopulation, such as B cell lymphocytes. For example, some methods obtain expression level results of all cell types in the cell mixture, and not that of a specific hematopoietic subpopulation.

Specifically, in the mathematical method of deconvolution (Lu et al.), the fractional proportion of each cell types is determined in a cell-mixture sample. The expression level of a gene in a particular cell type in a group of samples is assumed to be a constant. The expression in a cell-mixture sample is simply determined based on the fractional proportion of a specific subpopulation in the sample, and is not a measure of the actual expression in the subpopulation of an individual, as it is assumed to be constant.

On the other hand, gene TA of specific hematopoietic subpopulation (e.g., a leukocyte subpopulation) are the preferred biomarkers. In order to obtain TA of a specific hematopoietic subpopulation, the current state of the art requires a prior cell separation or cell sorting to isolate the specific hematopoietic subpopulation from peripheral whole blood sample before quantitative analysis of gene expression. Cell subpopulations separation is laborious and tedious. Such procedure is basically not practical in the setting of a clinical service laboratory. Thus, there are limitations in current methods of analysis of gene expression in peripheral blood samples.

Extensive research has been carried out to study the gene expression level in purified hematopoietic (specifically leukocyte) subpopulations. They are carried out after procedures of cell separation or cell culture in order to obtain samples of a specific leukocyte subpopulation that is under research. There has also been a strong interest to examine the gene expression levels in different types of peripheral blood samples, including whole blood and peripheral blood mononuclear cells samples as biomarkers of diseases, treatment response, and prognostic markers.

Therefore, it is desirable to provide new methods, apparatuses, systems, and compositions to eliminate the requirement of cell purification or separation in the process to determine the levels of gene expression or TA of target genes in a specific hematopoietic subpopulation (e.g., leukocyte cell-type), as well as provide other advantages.

BRIEF SUMMARY

Embodiments can provide methods, systems, and compositions to determine gene expression level (transcript abundance) of a specified cell-type subpopulation by analysis of a cell mixture sample composed of multiple subpopulations of various cell-types without the need of prior separation of the component cell-type subpopulations. For example, a target gene and a reference gene can be identified as being informative for a specific cell-type subpopulation. A gene can be defined as being informative for a subpopulation when at least 50% of the gene's transcripts (or other percentage greater than 50%) in the cell mixture are from the subpopulation. Informative genes can be identified from calibration experiments that may involve isolating subpopulation, but such experiments can be performed by a creator of an assay, and not during production runs. A relative abundance between the informative target and reference gene in the cell mixture can be used as a biomarker, e.g., as equivalent to the relative abundance in a sample of isolated cells of the subpopulation. As described herein, this relative expression level in the cell mixture of the informative target and reference genes can correlate to the relative expression when measured in the isolated subpopulation. Thus, a similar biomarker can be obtained without the difficult step of isolating the cells of the subpopulation.

According to one embodiment, a method measures a genomic expression in a first subpopulation of cells of a cell mixture containing a plurality of subpopulations. A plurality of subpopulation informative genes are identified, and include at least one subpopulation target gene and at least one subpopulation reference gene having a lower biological variation relative to the subpopulation target gene. Each of the plurality of subpopulation informative genes are identified as having at least a predetermined percentage of its transcripts in the cell mixture contributed by the cells of the first subpopulation, where the predetermined percentage is equal to or greater than 50%. A computer system determines a first amount of transcripts of the at least one subpopulation target gene in the cell mixture and a second amount of transcripts of the at least one subpopulation reference gene in the cell mixture. A parameter that is a relative value of the first amount to the second amount is calculated. The parameter conveys an amount of genomic expression of the subpopulation target gene in the first subpopulation.

According to another embodiment, a method identifies a subpopulation reference gene for a first subpopulation. Data regarding which of a plurality of genes are expressed in the first subpopulation of cells in a plurality of cell-mixture samples are received. A first set of genes that are expressed in the first subpopulation of cells are identified based on the data. A computer system analyzes the data to determine a respective expression level for each of the first set of genes in each of a plurality of first subpopulation samples. Each first subpopulation sample is from a different cell-mixture sample of a different subject. A subset of subpopulation genes that each have at least a predetermined percentage of their respective transcripts in the plurality of cell-mixture samples contributed by the cells of the first subpopulation is identified using the respective expression levels. The predetermined percentage is equal to or greater than 50%. Respective expression levels of the subset of subpopulation genes are analyzed to identify at least one subpopulation reference gene that has a variance of expression levels among the first subpopulation samples of less than a threshold.

According to another embodiment, a kit for measuring a genomic expression in a first subpopulation of cells of a cell mixture containing a plurality of subpopulations is provided. The kit includes primers for a plurality of subpopulation informative genes. The primers include at least one first oligonucleotide for specifically hybridizing to at least a section of a transcript of a subpopulation target gene, and at least one second oligonucleotide for specifically hybridizing to at least a section of a transcript of at least one subpopulation reference gene having a lower biological variation relative to the subpopulation target gene. Each of the plurality of subpopulation informative genes are identified as having at least a predetermined percentage of its transcripts in the cell mixture contributed by the cells of the first subpopulation. The predetermined percentage is equal to or greater than 50%.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 1A shows examples of proportions of a specific leukocyte subpopulation among nucleated cell populations in peripheral whole blood (WB) sample. FIG. 1B shows examples of proportions of a specific leukocyte subpopulation among nucleated cell populations in peripheral blood mononuclear cell (PBMC) sample.

FIG. 4A shows a table 400 of results for hematopoietic subpopulations in peripheral whole blood samples according to embodiments of the present invention. FIG. 4B shows a table 450 of results for hematopoietic subpopulations in peripheral blood mononuclear cells samples.

FIG. 8A shows a table 800 of observed differential expression (X, folds difference) in TA between B cells subpopulation fraction sample and average whole blood sample according to embodiments of the present invention. FIG. 8B shows a table 850 of genes (as determined from table 800 of FIG. 8A) that fulfill the criteria for X50 according to embodiments of the present invention.

FIG. 10A shows a table 1000 about the comparison of gene expression levels between CD3+ve total T cells and whole blood samples collected from each individuals. The values (X) represent the differential expression levels in term of number of folds higher in the cell subpopulation than in whole blood sample. The data is used to evaluate for X50 criteria of subpopulation information genes. FIG. 10B shows a table 1050 of variance of TA for identification of subpopulation reference gene. FIG. 10C shows a table 1060 of the performance of Direct LS-TA assays by correlations with expression levels of target genes in enriched CD3+ve total T cells (gold standard method) and the effect of using two subpopulation reference genes. Degree of correlation is expressed as $R^2$, coefficient of determination

FIG. 12A shows a table 1200 about the comparison of gene expression levels between granulocytes and whole blood samples collected from each individuals. The values (X) represent the differential expression levels in term of number of folds higher in the cell subpopulation than in whole blood sample. The data is used to evaluate for X50 criteria of subpopulation information genes. FIG. 12B shows a table 1250 of variance of TA of genes in separated granulocyte samples for identification of subpopulation reference gene. FIG. 12C shows a table 1260 of the performance of Direct LS-TA assays using different subpopulation reference genes by their correlations with results by gold standard method (TA in separated granulocyte samples). Degree of correlation is expressed as $R^2$, coefficient of determination.

DEFINITIONS

Figure 2:
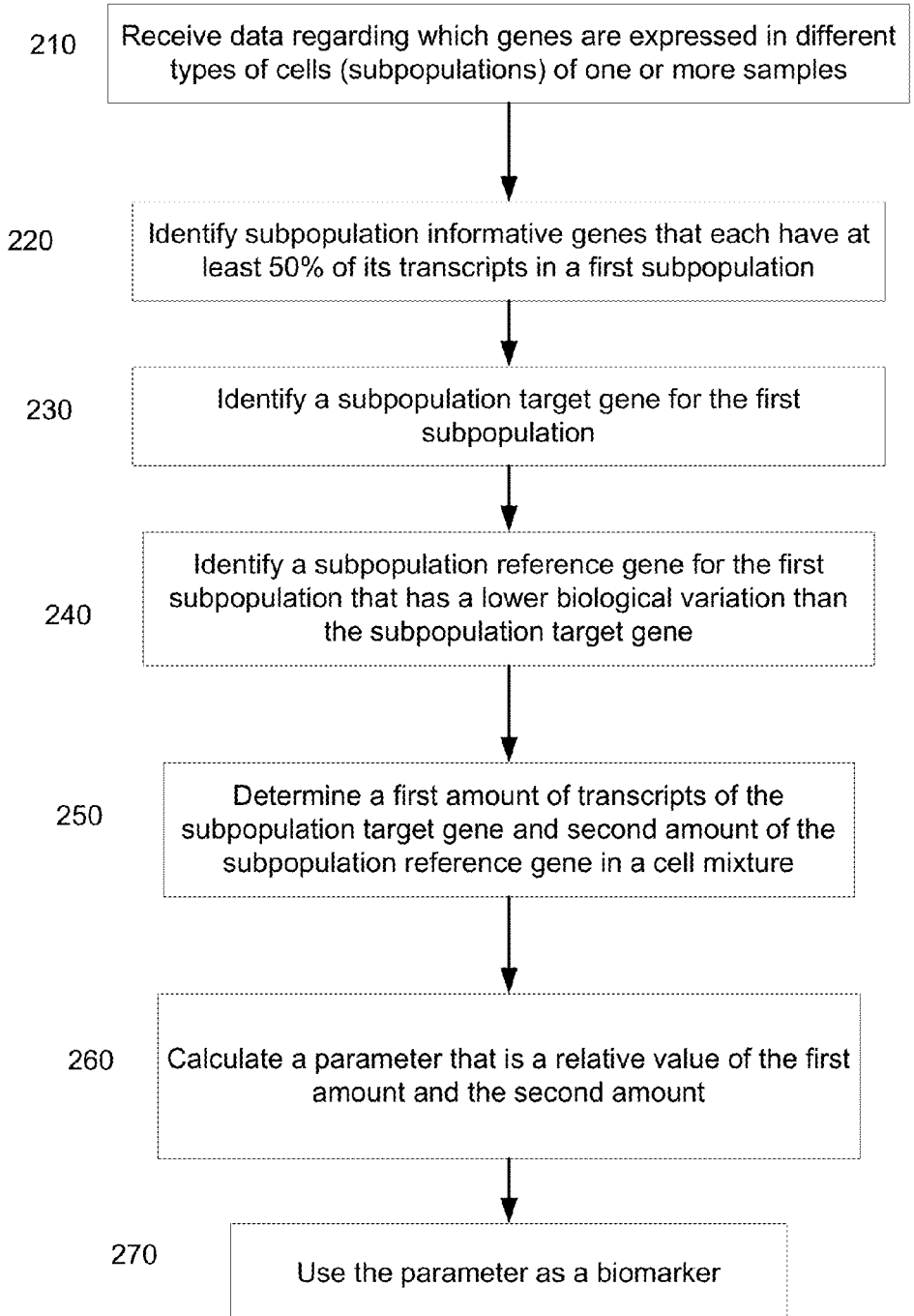
FIG. 2 is a flowchart illustrating a method 200 for measuring a genomic expression in a first subpopulation of a cell mixture containing a plurality of subpopulations according to embodiments of the present invention.

Hematopoietic subpopulations refer to the cellular composition of blood and consists of cellular population of different cell types which are broadly divided into red blood cells, white blood cells (leukocytes), and platelets. Leukocytes represent the majority of nucleated cellular population of blood. Leukocytes include different cell types that have specific functions and characteristics, such as neutrophils, lymphocytes, monocytes, eosinophils, basophils, and natural killer cells.

The following leukocyte subpopulations are examples. Granulocytes (polymorphonuclear leukocytes) are characterised by the presence of cytoplasmic granules in their cytoplasm. Neutrophils, basophils, and eosinophils, are the three type of granulocytes. Neutrophils accounts for ~90% of all granulocytes. Lymphocytes are involved in immune responses. They are classified into T cells and B cells which are responsible for different immune mechanisms, cell-mediated immunity, and antibody production. T cells are further divided into CD4 and CD8 T cells also called T helper cells and T cytotoxic/suppressor cells. Natural killer cells are a special form of lymphoid cells that is involved in innate immunity. Monocytes are macrophages in transit in the circulation, and are involved in antigen presentation and phagocytosis.

The direct leukocyte subpopulation specific transcript abundance assay (Direct LS-TA), as described herein, determines the transcript abundance (TA) of target gene(s) in one leukocyte subpopulation without the need of prior cell separation to isolate the subpopulation cells from the blood sample. For example, if the subpopulation is B lymphocytic cells, the assay could be denoted as Direct LS-TA for B cells. The Direct LS-TA for B cells can determine the abundance directly from a cell mixture sample, such as peripheral whole blood sample, without cell separation to isolate the B cells. This new Direct LS-TA method disclosed here can rely on quantification of two subpopulation informative genes.

Subpopulation informative genes (also referred to as subpopulation genes) refer to any gene with at least 50% (or other percentage greater than 50%) of its transcripts in a cell-mixture that are contributed by a single leukocyte subpopulation or cell-type. Two types of subpopulation genes are a subpopulation informative target gene and a subpopulation informative reference gene.

Subpopulation informative target genes (also referred to as subpopulation target genes) are selected among subpopulation informative genes identified for a specified subpopulation. These genes may be involved in a certain pathway of interest, may be differentially expressed in healthy subjects and patients, or may be co-expressed with other gene of interest.

Subpopulation informative reference genes (also referred to as subpopulation reference genes) are selected among subpopulation informative genes identified for a specified subpopulation. They show a low level or the least extent of biological variation among identified subpopulation genes of a specific subpopulation.

DETAILED DESCRIPTION

Peripheral blood is composed of different hematological cell-types including red blood cells (RBC) and various leukocyte subpopulations which are present in different proportion. The gene expression level in an individual leukocyte subpopulation (e.g. granulocytes, lymphocytes) in blood circulation is highly promising as an informative biomarker. Current measurement of transcript abundance (TA) in blood sample as disease biomarkers do not quantify TA in a specific hematopoietic subpopulation, or have to isolate cells of the specific hematopoietic subpopulation as part of the production run to quantify TA. Embodiments avoid a cell separation step and can determine gene expression level of a specific cell type directly in a cell mixture sample by identifying and using subpopulation genes that express more than 50% (or other percentage greater than 50%) in the specific hematopoietic subpopulation. One example is the direct LS-TA assay described herein.

Embodiments can use a relative transcript abundance (e.g., of just one gene or a summative index for multiple genes) of one or more subpopulation informative target gene gene(s) relative to one or more subpopulation informative reference gene(s) as the quantitative measure of gene expression level of the target gene in the specified cell-type subpopulation. Examples demonstrate that this relative abundance of an informative target gene (i.e. informative for the specified subpopulation) as measured in a peripheral blood sample correlates with the gene expression levels of the target gene in the specified subpopulation fraction obtained by cell separation, such as magnetic cell sorting. Therefore, it is demonstrated that transcript abundance of a specified leukocyte subpopulation can be determined without the need of prior cell separation.

Potential applications of embodiments are widespread as they can allow determination of gene expression of a specific hematopoietic subpopulation in peripheral blood samples. For example, such a measured relative abundance of subpopulation genes (as described herein) are useful as biomarkers for diagnosis and prognosis of autoimmune diseases, infectious illness, chronic diseases, acute injuries, septic shock, acute organ failure or pathologic conditions associated with altered gene expression in hematopoietic subpopulation cells. In addition, embodiments can be useful in identifying pharmacogenetic biomarker for monitoring of treatment response of immunosuppressive drugs, or other drugs that are associated with altered gene expression in hematopoietic subpopulation cells. In applications in tissue biopsy of solid organs, examples include but not limited to gene expression of malignant cells or various infiltrative lymphoid cell subpopulations in tissues of solid organs like kidney, liver, skin etc.

I. Subpopulations in Different Blood Samples

Peripheral blood is composed of different hematological subpopulations (cell-types) which are present in different proportions among the nucleated cell population of whole blood. The red blood cell and leukocytes are major lineages. The leukocytes are further composed of different subpopulations. For example, B cell lymphocytes account for about 5% and granulocytes account for up to 65% of nucleated cells in peripheral whole blood.

Examples of hematopoietic subpopulation include but not limited to various hematological cell-types or leukocyte subpopulations such as lymphocytes, granulocytes, T lymphocytes and B lymphocytes that constitute at various proportions of the cellular component of peripheral blood, which is an example of cell mixture sample. Cell mixture samples of peripheral blood include but not limited to whole blood, processed whole blood, or peripheral blood mononuclear cells samples. Other than a hematologic sample, a tissue biopsy is another example of cell mixture sample to which embodiments can also apply.

Different leukocyte subpopulation cells are present in different proportions in peripheral blood and the proportional cell count is higher than 5%. There are established reference ranges of such proportion available from standard hematology textbooks. FIG. 1A shows a table 100 of examples of proportions of a specific leukocyte subpopulation among nucleated cell populations in peripheral whole blood (WB) sample. FIG. 1B shows a table 150of examples of proportions of a specific leukocyte subpopulation among nucleated cell populations in peripheral blood mononuclear cell (PBMC) sample.

It is clear from these two tables that the listed hematopoietic subpopulations represent 5% to 65% of the total nucleated cells in peripheral blood samples. Therefore, the proof of principle and utility of experiments was carried out using an example of a hematopoietic subpopulation representing 5% in a peripheral blood sample. Results below demonstrate that embodiments can determine hematopoietic subpopulation specific gene expression for a subpopulation present at 5% of a cell-mixture sample. Therefore, other cell-type or subpopulation present at higher proportions can be targeted by embodiments described herein. Additionally, since 5% is a relatively low percentage, hematopoietic subpopulations present at below 5% may also be handled according to embodiments. The leukocyte subpopulation of interest may be, for example, lymphocytes, B cells, T cells, neutrophils, granulocytes, monocytes, eosinophils etc. Other examples are cell-type subpopulations in tissue biopsies, like infiltrating lymphoid cells in various organs.

II. Measuring Expression Levels

The expression level of a particular gene can provide a useful biomarker. For example, the expression level (also referred to as transcript abundance) can be compared to a cutoff value to determine a classification for diagnosis and prognosis. Some current methods determine the expression level for a particular gene across all subpopulations in a cell mixture (as is described in section A below). However, such biomarkers can be inaccurate since changes in expression levels can result from various factors, some of which are not indicators of disease or other condition. Other current methods (section B) isolate cells of a particular subpopulation to obtain more accurate biomarkers; however, the act of isolation is difficult and costly. Section C introduces techniques of the present invention.

A. Across All Cell Types (Subpopulations)

Typical methods determine quantifications of transcript abundance (TA) contributed by all the various cell-types present in cell mixture samples. For example, a universal housekeeping gene can be used as an internal reference gene in a relative quantification technique such as quantitative PCR (QPCR). As another example, a microarray can be used to quantify gene expression in a cell mixture sample, with the data being normalized in a global way that is not specific to a cell-type or leukocyte subpopulation in the cell-mixture sample. As another example, sequencing technology can be used to quantify gene expression in a cell mixture, with the data again being normalized in a global way that is not specific to a cell-type or leukocyte subpopulation in the cell-mixture.

Such methods are carried out with a mixture sample of different cell subpopulations in peripheral blood such as peripheral whole blood (WB) samples or peripheral blood mononuclear cells (PBMC) samples. The results obtained by these existing methods are limited by (a) they are not specific to any hematopoietic subpopulation and (b) the results are influenced by proportions of various hematopoietic subpopulations present in such cell mixture samples of peripheral blood. Thus, all such methods do not provide an assessment or quantification of TA of a specific hematopoietic subpopulation in a cell-mixture samples. These prior art biomarkers can only quantify total TA contributed from all the various cell-types present in cell mixture samples, and do not represent the TA of a specific hematopoietic or leukocyte subpopulation.

Transcript abundance in whole blood samples or cell mixture samples are affected by at least two factors: (1) proportion of various cell subpopulations in the samples and (2) transcript abundance in each individual cell subpopulations (Fan and Hegde 2005). In most instances, the biological and clinically relevant question about change in transcript abundance is related to factor number (2), i.e., the change in transcript abundance in a specific hematopoietic subpopulation. Therefore, any change in transcript abundance in a cell mixture sample cannot be directly attributed to an underlying change in transcript abundance in the hematopoietic subpopulation of interest.

The determination of transcript abundance in a specific leukocyte subpopulation instead of the whole blood sample or other cell mixture can eliminate the confounding on transcript abundance measured in the cell mixture due to difference in composition of various leukocyte subpopulations. Embodiments of the present invention are readily translated to assay kits for such a purpose and applied to quantify these subpopulation specific biomarkers in a variety of clinical settings.

B. Of a Particular Subpopulation by Separation

As mentioned above, existing methods determine gene expression in peripheral blood samples using universal housekeeping genes as the reference gene (e.g. beta-actin, GAPDH, ribosomal protein genes). Similarly, various approaches of global non-specific normalization of data were used for analysis of large scale expression data like microarray and sequencing. However, these reference genes and non-specific normalization approaches are not specific to any hematopoietic or cell-type subpopulation in cell mixture samples. Therefore, the relative abundance of gene expression determined from a peripheral whole blood sample or other cell mixture sample by existing methods only represent cell count weighted average expression of target gene of all the various cell-types present in the mixture sample of peripheral blood.

Thus, such assays of gene expression in a cell mixture sample produce confounded results as it is not certain whether the differential gene expression is due to: pathology in a single cell type, simultaneous changes in multiple cell types, or change in counts of various cell types when different cell subpopulations have different levels of gene expression. Therefore, current methods use cell sorting, isolation, or separation to obtain an enriched sample of a specific cell subpopulation to determine the alternation of cell specific gene expression. However, isolation of cells is difficult and costly.

The current standard approach and gold standard is comprised of (1) a cell isolation procedure to obtain a sample that is enriched for a particular cell type of interest and (2) measurement of gene expression level in the enriched samples for cell type of interest. After isolation of cell type of interest, RNA is extracted, then it may be followed by the step of reverse transcription. Afterward, measurement of gene expression (transcript abundance, TA) can be performed by one of the prevailing methods, like real-time quantitative PCR, microarray, sequencing or other methods Cell sorting or isolation can be performed by various approaches, including: (1) density gradient, e.g. Ficoll is used to separated PBMC and granulocytes; (2) Fluorescence activated cell sorting (FACS) in which cell type specific surface markers are bound to fluorescent labeled antibodies and sorting is performed by flow cytometer with electromagnetic mechanisms; (3) Magnetic activated cell sorting (MACS) in which cell type specific surface markers are bound to magnetic bead linked antibodies and cell of interest can be isolated by passing the sample through a magnetic field. More recently, microfluidic methods have also be explored to provide the cell isolation function to obtain a cell-type enriched sample from a cell-mixture sample C. Of a Particular Subpopulation without Separation As described above, it is desirable to evaluate cell type specific gene expression directly in a cell mixture sample without the need of prior cell sorting. Embodiments bypass the requirement of prior cell separation and allow direct determination of cell-type subpopulation specific gene expression directly in a cell mixture sample. Embodiments use selected cell-type informative reference genes and cell-type informative target genes to determine the gene expression level (e.g. TA) of a particular specified hematopoietic or cell-type subpopulation in a cell mixture of peripheral blood. Embodiments can also be applied to solid tissue cell mixture samples like tissue biopsies.

Examples below use B lymphocytes as the subpopulation of interest. B lymphocytes represent 5% of the total leukocyte population in peripheral whole blood. Thus, this example serves to demonstrate that embodiments are also applicable to other leukocyte subpopulation present at proportional cell count of 5% or above in a cell-type mixture sample. Such situations include but not limited to: (1) Natural killer cells in peripheral whole blood sample; (2) CD4 T cells in peripheral whole blood sample; (2) CD8 T cells in peripheral whole blood sample; (3) monocytes in peripheral whole blood sample; (4) neutrophils/granulocytes in peripheral whole blood sample; (5) eosinophils in peripheral whole blood sample; (6) Natural killer cells in peripheral blood mononuclear cell preparations; (7) CD4 T cells in peripheral blood mononuclear cell preparations; (8) CD8 T cells in peripheral blood mononuclear cell preparations; (9) monocytes in peripheral blood mononuclear cell preparations; and (10) B cells in peripheral blood mononuclear cell preparations Advantages of various embodiments of this invention can include, without limitation: (1) no prior cell separation, enrichment, or sorting is required; (2) no requirement to obtain the cell counts per unit volume of each hematopoietic subpopulation or leukocyte subpopulation; (3) applicable in the setting of quantitative PCR in which only few transcripts are quantified in each sample; (4) applicable in setting when multiple subpopulation informative genes (target genes, reference genes or both) are quantified by various methods, including but not limited to quantitative PCR, microarray, sequencing, or other molecular counting methods like digital PCR; and (5) applicable to large scale transcript abundance data generated from microarray in which hundreds to tens of thousands transcripts are quantified in each sample.

II. Method

Figure 3:
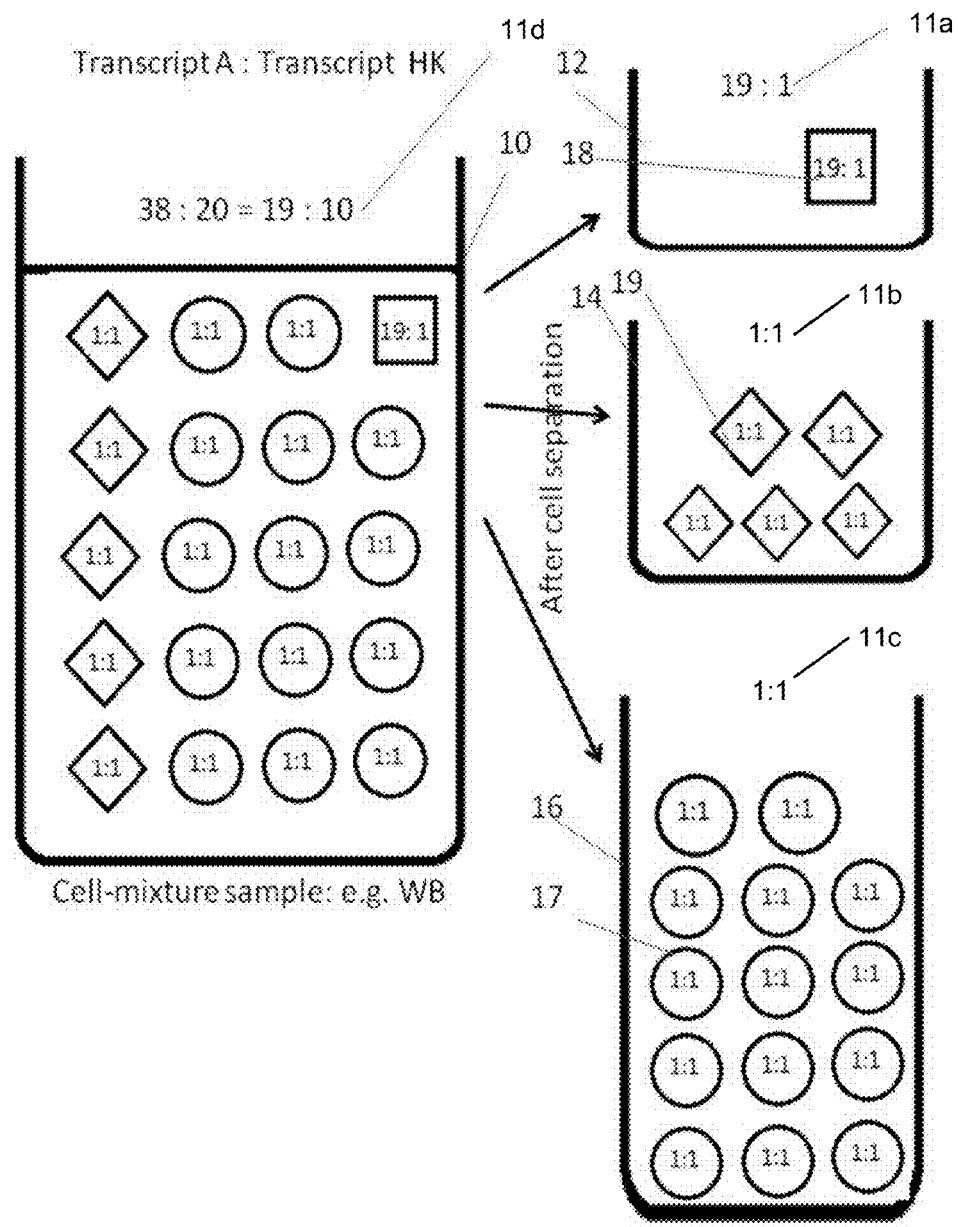
FIG. 3 shows a hypothetical example about a cell-mixture sample to establish properties used for selection of cell-type subpopulation informative genes when gene expression measurements are available in a specified subpopulation and the cell-mixture sample of interest according to embodiments of the present invention.
Figure 5:
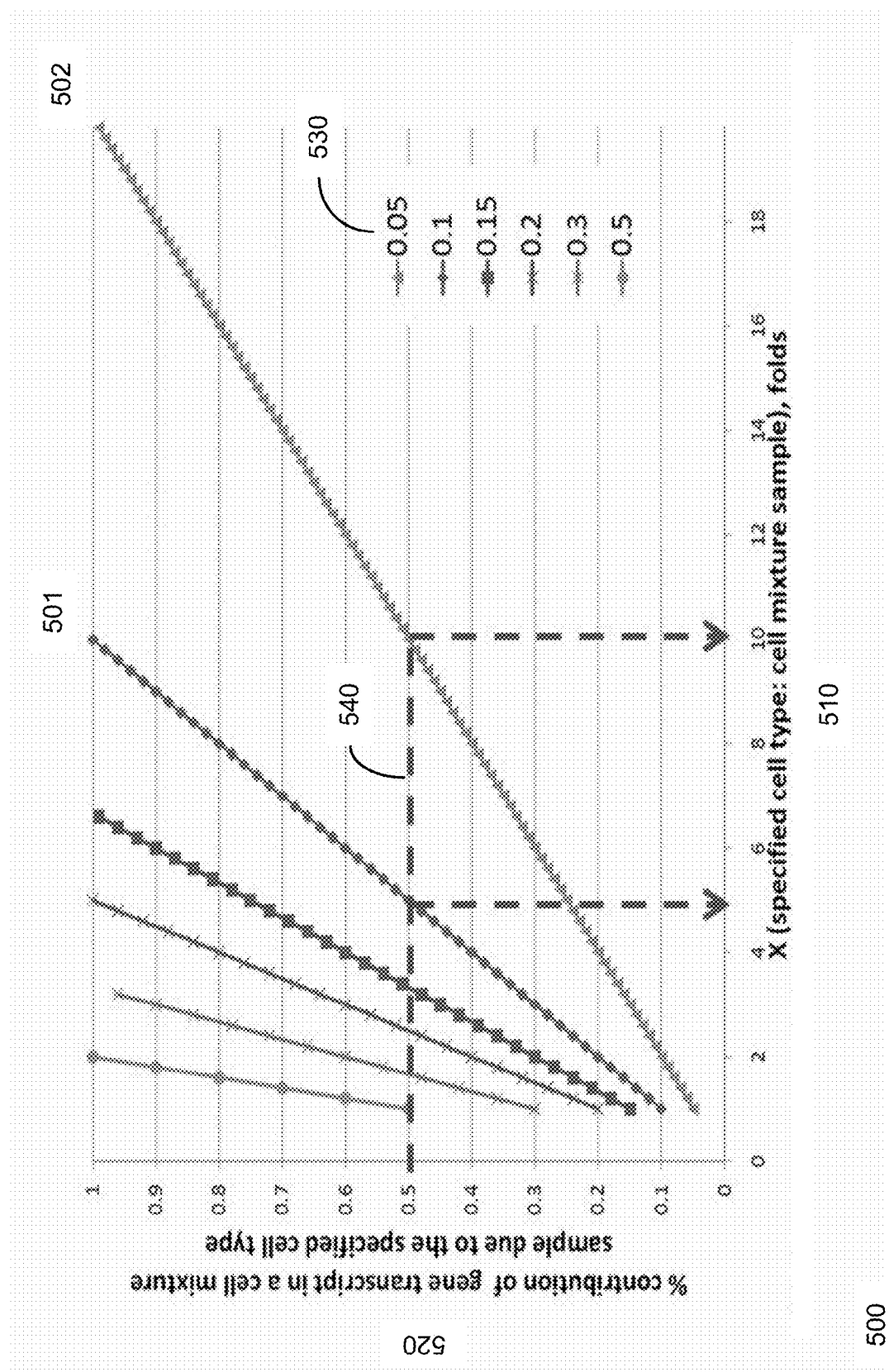
FIG. 5 is a graph 500 showing the relationship between percentage contribution of a transcript in a cell mixture sample by a specified cell-type subpopulation and folds difference of TA in specified cell-type subpopulation fraction over TA in the cell mixture sample (X) for subpopulations of various proportional cell count from 0.05 (5%) to 0.5 (50%) according to embodiments of the present invention.

Subpopulation informative genes are defined as those genes where at least 50% (or other higher percentage) of the total amount of its transcript in the cell mixture sample is contributed by the specified cell-type subpopulation. Embodiments can use criteria to select such subpopulation informative genes based on different scenarios, e.g., when expression level data are available for both the specified cell-type fraction and cell mixture samples (as shown in FIG. 3), or when expression level data are available only for the specified cell-type fraction and some other cell fractions but not available for the cell mixture sample (as shown in FIGS. 4 and 5).

Once a subpopulation informative target gene is chosen, its expression level (e.g., TA) in a cell mixture sample can be quantified relative to that of a subpopulation informative reference gene. As the transcripts of both of these genes form a majority in the cell mixture, the expression level in the mixture can be used like a biomarker for expression levels in the isolated subpopulation. The methods of quantification of TA include but not limited to quantitative PCR, microarray, sequencing, or hybridization or other methods suitable for quantification of gene transcripts.

FIG. 2 is a flowchart illustrating a method 200 for measuring a genomic expression in a first subpopulation of a cell mixture containing a plurality of subpopulations according to embodiments of the present invention. Cells of the first subpopulation are not isolated prior to the measurement. Instead, particular genes are identified as being informative for the first subpopulation, thus not just any gene can be used in method 200. The level of genomic expression for the informative target gene can be normalized with respect to a reference gene that is also informative for the first subpopulation. The level of expression (which can be expressed as a numerical parameter) can be used as a biomarker for diagnosis. Some of the steps below can be performed as part of manufacturing an assay, and other step performed by a user of the assay. Not all steps are performed in every embodiment related to method 200. Some or all of the steps may be performed by a computer system.

In step 210, data regarding which genes are expressed in different types of cells (subpopulations) of one or more samples is received. The data can be obtained from samples taken from multiple organisms (e.g., from multiple people or same type of animal or plant). The data can provide a transcript abundance (TA) of a gene for each subpopulation. The data may be generated by isolating a subpopulation of cells and then quantifying the transcripts, e.g., by methods known to one skilled in the art, such as quantitative polymerase chain reaction (QPCR). A computer system can use the data to determine a relative and/or absolute quantity of transcripts for each subpopulation. The data can also specify the fraction of cells in a mixture that are from each subpopulation.

In one embodiment, step 210 can be performed by a manufacturer of an assay for measuring the genomic expression, as opposed to being performed by a technician using the assay. Thus, the isolation would be performed only once to identify informative genes, but need not be repeated after the informative genes are identified. In another embodiment, the data can be obtained from another entity, e.g., where the data is published in a paper, in a pamphlet as part of a kit, or via a display produced by software.

In some embodiments, gene expression data is obtained for just a first subpopulation in a cell-mixture sample. For example, one can be obtain gene expression data conveying the expression of a plurality of genes in the first subpopulation. Additionally, the expression of these genes in the entire cell-mixture sample can also be obtained. In other embodiments, the expression of a plurality of genes is obtained for a plurality of subpopulations in the cell-mixture sample, but no data is obtained for the expression in the entire cell-mixture sample.

In step 220, a plurality of subpopulation informative genes are identified, e.g., using the expression data from step 210. A subpopulation informative gene is identified as having at least a predetermined percentage of its transcripts in the cell mixture contributed by the cells of the first subpopulation. The predetermined percentage is equal to or greater than 50% (e.g., 50%, 60%, 70%, 80%, 90%, or any percentage less than 100%). For example, a subpopulation gene can have at least 50% of its transcripts (e.g. mRNA) contributed by the cells of the first subpopulation.

In one embodiment, the identification can simply be obtaining these genes from a list. For example, a kit or instructions for a particular diagnostic test could specify a list of genes for a particular subpopulation. Thus, the identification can be performed by a clinical lab technician and/or software that receives a list of subpopulation informative genes. The identified genes could be all of the genes of a list or just some of the genes (e.g. by some selection mechanism, which may occur based on the diagnostic test to be performed), e.g., the genes mentioned in steps 230 and 240 below.

In another embodiment, the identifying may be more complicated. For example, the identifying may be performed by a research lab that designs tests while some later steps may be performed by a clinical lab (e.g. the simple receiving of a list, as mentioned above). In one implementation, the data is analyzed by a computer system to determine expression levels of different genes in particular subpopulations of cells relative to a housekeeping gene, which has a uniform expression over many cell types (e.g. all cell types in a cell mixture).

The percent contribution of a gene transcript in a cell mixture sample due to the specified cell type (e.g. the first subpopulation) can be used to identify a necessary differential expression ratio X of that gene by comparing the purified subpopulation cell fraction and cell mixture samples. X is the multiple of gene expression level in the specified cell subpopulation relative to the cell mixture sample, e.g., a value of 10 means the gene is expressed by specified cell type 10 times (fold) higher than that in the cell mixture sample. FIG. 4 shows a chart for various percentages of the specified cell type; FIG. 4 is described in more detail later.

In step 230, a subpopulation target gene is identified, e.g., from a list of subpopulation informative genes. Typically, the target gene is one that is known or hoped to be correlated to a particular condition, e.g., a disease state. During initial analysis, the correlation may not be known. But once correlation is known, the identified target gene can be used in a diagnosis. In one embodiment, a computer system can identify the subpopulation target gene by receiving a selection of the target gene from a user or as specified in an input file.

In step 240, a subpopulation reference gene is identified. A computer system can identify the reference gene in a similar as the target gene was identified. In one embodiment, the subpopulation reference gene has a lower biological variation relative to the subpopulation target gene. The variation can be just in the first subpopulation or the cell mixture. Measurements across various samples from various subjects can be used to determine the variation. A computer system can analyze the data from the various samples to determine the biological variation of the level of expression of the reference and target genes, which can be determined with respect to a housekeeping gene. In various implementations, the variation can be evaluated as coefficient of variation which can be less than 200%, less than 100% (or 90%, 80%, 70%, 60%, 50%, 40%, 30%, 20%, 15%, 10%, or 5%).

In one embodiment, the subpopulation target gene and the subpopulation reference gene can be chosen so as not to have appreciable expression levels in specific subpopulations, e.g., red blood cells or platelets. In another embodiment, the red blood cells and platelets can assumed to be filtered out of the cell mixture, and thus their contribution to TA can be removed in determining an informative gene.

In step 250, a computer system determines a first amount of transcripts of the subpopulation target gene in a cell mixture and a second amount of transcripts of the subpopulation reference gene in the cell mixture. The first and second amounts can provide a quantification of transcript abundance for the two genes. The cell mixture can be a sample taken from a patient for analysis by a lab.

The computer system can determine the amounts based on data (e.g., signals) received at the computer system. For example, the computer system could receive fluorescent signals (or other signals detected from one or more reactions involving the cell mixture), and convert these signals into the amounts (e.g., using CT techniques). The fluorescent signals could be converted to digital information and then received at the computer system, which can then use the digital information to determine the amounts. Other examples include the computer receiving sequencing data or microarray data.

The amount of transcripts of a gene can be measured via numerous mechanism as will be known to one skilled in the art. Signals (e.g., fluorescent signals) can be measured from reactions (e.g., PCR or sequencing reactions) and these signals can be used to determine the amounts of a transcript. For example, quantitative PCR can be used to obtain amplification curves, with CT methods being used to determine the amount from the amplification curve. Other measurements besides fluorescence from QPCR can be used to determine the amounts, such as microarray, sequencing, and hybridization. The measurement can be performed by a machine that is part of or communicably coupled to the computer system.

In step 260, a parameter is calculated from the first amount and second amount. In one aspect, the parameter is a relative value (e.g., relative abundance) of the first amount to the second amount. For example, the parameter can be a simple ratio of the two amounts. Other examples are complex functions with the amounts as inputs (e.g. as inputs to respective functions) and ratios of functions may be used to determine the parameter. The parameter conveys an amount of genomic expression of the subpopulation target gene in the first subpopulation. The parameter may not be the most accurate measure (e.g., relative to a measurement obtained from an isolated cell fraction), but it can still provide a measure, as shown in the correlation analysis below, and is more efficient to determine.

In step 270, the parameter is used as a biomarker. For example, the parameter can be compared to one or more cutoff values to determine a classification of the cell mixture. The classifications can include whether the cell mixture (and therefore the patient) is in a diseased state or a non-diseased state. A range of values can be associated with the non-diseased state. Another classification can be non-classified or indeterminate. For example, a particular range can be indeterminate; additional testing can be performed for an non-classified sample. A more expense technique using isolation of cells of the subpopulation could then be performed for the few samples that are indeterminate in order to get a more accurate measurement.

As described above, overexpression of a target gene in peripheral blood is high could be due to (A) average expression of such gene in some specific cell-types component is increased and/or (B) number or proportion of those cell-types component is increased. Average expression of such gene in a specific cell-types is the biological index useful as biomarker. However, it is confounded by number or proportion of the specific leukocyte subpopulation present in the mixture sample. Although the exact value of expression of such gene in a specific cell-type is not exactly determined without prior cell separation, the new parameter disclosed here correlates with the exact value, as is shown below. Thus, the measurement obtained with the parameter is an estimate of the exact value, albeit an estimate that more efficient to determine.

Thus, embodiments can bypass the requirement of prior cell separation and allow determination of leukocyte subpopulation specific gene expression directly in peripheral whole blood. Potential applications are widespread. For example, diagnosis of autoimmune diseases, determination of effect of immunosuppressive drugs, diagnosis of infectious illness. A specific example is differentiation of infection pathogens or as prognosis biomarkers in patients with fever. Current methods use protein biomarker in blood (like C-reactive protein, CRP) to differentiate patients who have a significant infection. However, CRP is not specific. Therefore, an assay of the gene expression of granulocyte in whole blood will be very informative. Other specific examples include use as biomarker to assess the pharmacodynamics of immunosuppressant therapy in patients after transplantation, and monitoring of disease activity in autoimmune disease.

Assay kits can be developed to quantify cell-type informative target gene(s) and cell-type informative reference gene(s) in cell mixture samples to determine cell-type specific gene expression levels. For example, embodiments can provide direct leukocyte subpopulation specific transcript abundance (Direct LS-TA) assay kits that are used to determine the transcript abundance of particular target genes in a specific hematopoietic subpopulation. Such cell-type informative target genes can be genes in a pathway, genes responsive to external stimulus or genes that are found differentially expressed in a purified cell population either at baseline condition or after stimulation.

Although the main examples herein are applied in a human sample, embodiments can be used for other species. Embodiments can also be applied to other cell mixture samples such as tissue biopsy sample when multiple cell-types are present. Also, the particular transcripts can vary, e.g., just microRNA or alternative splicing transcripts. A sample can be an ex-vivo stimulation sample. In such situation, a peripheral blood sample is incubated with some stimuli for a specified period of time. Gene expression analysis is carried out after stimulation to determine the response.

III. Determining Informative Genes

As described above, embodiments use informative genes to obtain a measurement of expression level specific to a particular cell subpopulation. Genes that are informative for a particular subpopulation allow the isolation of those cells to be skipped, and a direct measurement made in the cell mixture to provide a measurement that is correlated with the measurement in the isolated cells. This section describes procedures for identifying informative genes (e.g., for step 220 of method 200), where the procedures may be performed by a manufacturer of an assay kit, so that the lab technician need not perform the analysis.

In one embodiment, gene transcripts expressed by a specified hematopoietic subpopulation or cell-type of interest contributing at least Y % (where Y is a predetermined percentage equal to or greater than 50%) towards the total amount of transcripts of such genes in a peripheral blood sample or cell mixture sample are useful and informative for quantification of transcript abundance of the specified hematopoietic subpopulation using the cell mixture sample. These transcripts are called cell-type informative transcripts and are from subpopulation informative genes. Examples of the predetermined percentage Y are 60%, 70%, 80%, 90% or 100%, or any percentage in between 50% to 100%, possibly including 50%.

In various embodiments, the identification of informative genes for a particular subpopulation can use the knowledge of the average percentage composition of a cell type in a cell mixture samples (e.g. whole blood), and the average gene expression levels of genes in all or most of the cell type subpopulations (e.g. granulocytes, B lymphocytes, etc.) or just one cell subpopulation and the entire cell mixture.

A. Expression Level Data are Available for Subpopulation and Cell Mixture

FIG. 3 shows a hypothetical example about a cell-mixture sample to establish properties used for selection of cell-type subpopulation informative genes when gene expression measurements are available in a specified subpopulation and the cell-mixture sample of interest according to embodiments of the present invention. This example represents the situation when TA data are available for cell-mixture sample 10 (an example of a calibration cell mixture) and some of the cell fractions 12, 14, or 16 after cell separation. Cell fractions 12-16 are samples of a single cell-type (subpopulation) obtained by cell separation procedures from cell-mixture sample 10.

In this cell-mixture sample 10 (e.g., peripheral whole blood or whole blood (WB)), there are hypothetically three types of cells, which are represented by different shapes including "square" 18, "rhomboid" 19 and "circle" 17. As shown, cell-mixture sample has 20 cells, where each instance of a shape represents one cell. Only three cell-types are depicted for simplicity, but the same principle holds for more cell-types.

Each subpopulation is present within a certain range of known proportional cell counts among all cellular components of the cell-mixture sample 10. Specifically, "square" cells 18account for 5% of the cells in the sample (1 in 20 cells), "rhomboid" cells 19 account for 25% of the cells in the sample (5 in 20), and "circle" cells 17 account for the remaining 70% of the cells in the sample (14 in 20 cells). These proportions are used as they represent typical proportions of various hematopoietic subpopulations in human blood samples.

The "square" cells 18 are the specified cell-type (subpopulation) of interest for which a cell-type informative TA assay is being developed. The ratios 11a-11c shown inside each cell fraction sample 12-16 represent the relative expression of transcript A (corresponding to gene A) to the transcript of a conventional housekeeping gene (HK) in a respective cell type. This is the gold standard method of quantification of gene expression level (specifically TA). The ratio 11d shown on the top of cell-mixture sample 10 represents the overall relative expression of transcript A to transcript HK in cell-mixture sample 10. Ratio 11d is obtained by counting all of the transcripts for gene A (which is 38) and the transcripts for the housekeeping gene (which is 20—one for each cell), thereby providing a ratio of 38:20, which is the same as 19:10. These ratios 11 are the quantities or expression data that are observed in experiment. The ratios 11 are also displayed within each cell.

To obtain the ratios 11a-11c, cell-mixture sample 10 can be separated to yield three purified cell fraction samples for each of the 3 cell-types 12, 14, and 16. A relative quantification of Transcript A 11 compared to the housekeeping gene is carried out the cell fraction samples. As only ratio 11a is needed to determine informative genes for population 18, only the square cells need to be isolated.

In one embodiment, a subpopulation informative gene has at least 50% of the total amount of the transcript in the cell mixture sample contributed by the specified cell-type subpopulation. Criteria can be provided to select such subpopulation informative gene based on the two expression data observed in the cell mixture sample 10 (ratio 11d) and the specified cell-type subpopulation fraction sample 12 (ratio 11a). This threshold ratio as the criteria for selection of cell-type informative genes is denoted as X50 ("square" cell:WB) as whole blood is used as an example of cell-mixture sample. Such threshold ratios X50 ("square" cell: WB) also applies to data of gene expression obtained by other methods like microarray or sequencing datasets where global normalization of intensity data is performed.

Based on the information in FIG. 3, 19 of transcript A can be attributed to subpopulation 18, and there are 38 transcript A in total in cell-mixture 10. Thus, 50% of Transcript A in the cell-mixture is contributed from the "square" cell-type 18. Therefore, transcript A fulfills the criteria of a cell-type informative transcript for "square" cell-type 18, and the corresponding gene is an informative gene for that subpopulation.

The analysis also shows that the relative expression of Transcript A to Transcript HK is 10 folds higher in the purified "square" cell sample 12 over the cell-mixture sample 10. It also indicates a gene with 10 folds higher relative expression in the purified cell fraction of interest fulfills the requirement of cell-type informative gene when the subpopulation comprises at least 5% of the cells in the cell-mixture.

B. General Formulation when Expression Available for Subpopulation and Mixture

A general formulation of the concept in FIG. 3 can determine whether a particular gene satisfies the X50 criteria based on the relative expression of gene A and gene HK in the cell-mixture and the isolated sample of a particular subpopulation. The selection of candidate cell-type informative genes applicable for cell-type informative expression analysis in cell mixture samples is based on the expression levels differences between the cell fraction sample of the specified cell-type and cell-mixture sample. Formulas for determining the threshold expression level for a subpopulation having a certain proportional cell count P are provided, as well as a graph showing the relationship of X-fold difference in expression level vs. the percentage of transcript in the cell-mixture for different proportional cell counts P.

The variable Etotal is the expression level (e.g., transcript abundance) of transcript A relative to transcript HK in the cell mixture. Etotal can be measured from the cell mixture using any suitable method (e.g., QPCR). The variable Ep is the expression level of the specified cell subpopulation (e.g. B lymphocytes, granulocytes, etc) for the selected gene relative to the HK gene. Ep can be measured from an isolated cell fraction of the specified subpopulation. The variable P is the proportional cell count of the specified cell subpopulation in the cell mixture. The variable X is the fold difference of TA of the selected gene in the specified subpopulation compared to TA in the cell mixture sample (e.g. whole blood), and thus X=Ep/Etotal.

The variable Eother is the average expression level of all other cells present in the mixture sample, e.g. whole blood samples, peripheral blood mononuclear cells samples. Eother is a weighted average based on the proportional cell count of each of the other subpopulation, and thus also applies when the expression levels are different among various other cell-types. In the equations below Eother is not actually determined, but simply used to determine the X required to satisfy the X50 criteria for a particular P.

All expression terms (E) are presented as an expression level of a transcript per cell and corresponds to the relative expression of transcript vs. conventional universal housekeeping gene. The variables relate to each other by the following equations:

$$Ep = X * Etotal \quad (1)$$

$$Etotal = P*Ep + (1-P)*Eother \quad (2)$$

$$Ep/X = P*Ep + (1-P)*Eother \quad (3)$$

$$Eother = \frac{Ep\left(\frac{1}{X} - P\right)}{(1-P)}. \quad (4)$$

The relationship between X and percentage contribution to total amount of transcripts in the cell mixture sample are shown in FIG. 5 for various values of P, which will be described further below. In the special case of 50% of the target transcript being contributed by the specified subpopulation P*Ep=(1−P)*Eother (5), where P*Ep is the amount of transcripts from the specified subpopulation, (1−P)*Eother is the amount of transcript from the other subpopulations, and they equal each other when both are 50%. Substituting equation (4) into equation (5) provides $$P*Ep = (1-P)\frac{Ep\left(\frac{1}{X} - P\right)}{(1-P)}, \quad (6)$$

which provides $$X = \frac{1}{2P}. \quad (7)$$

Thus, for the specified cell-type to contributes 50% (X50 criteria) of the total amount of a transcript in the cell mixture, the folds difference X of gene expression or TA in these two samples (i.e. the isolated subpopulation relative to the cell mixture) has to be equal to or larger than (½P). For example, if the subpopulation makes up 5% of the cell mixture, then X must be at least 10, which is as shown in FIG. 3. This X50 value of folds difference is used as a criteria for identification of subpopulation informative genes. One may read out X value for any desirable percentage contribution by a subpopulation of interest from FIG. 5, which will be described in details below.

FIG. 4A shows a table 400 of results for hematopoietic subpopulations in peripheral whole blood samples according to embodiments of the present invention. Column 410 lists different subpopulations of peripheral whole blood. Column 420 shows values of proportional cell count (P) for each specified cell subpopulation, as obtained from standard book and laboratory reference ranges. Column 430 shows the fold difference X required to satisfy the criteria of 50% or more of the transcripts for a gene to come from the subpopulation. As you can see, the value of X is equal to ½P.

FIG. 4B shows a table 450 of results for hematopoietic subpopulations in peripheral blood mononuclear cells samples according to embodiments of the present invention. Column 460 lists different subpopulations of peripheral blood mononuclear cells. Column 470 shows values of proportional cell count (P) for each specified cell subpopulation, as obtained from standard book and laboratory reference ranges. Column 480 shows the fold difference X required to satisfy the criteria of 50% or more of the transcripts for a gene to come from the subpopulation. As you can see again, the value of X is equal to ½P.

Columns 430 and 480 of the tables are used as threshold values of the criteria to identify cell-type informative genes. For example, B lymphocytic cells informative transcripts are selected among those that are expressed at least 10 times higher in the B cell fraction sample than an average whole blood sample for peripheral whole blood, as shown in FIG. 4A. These values are denoted as X50, X for 50% contribution solely by a single subpopulation. In other words, X50 is the fold difference of TA of specified cell fraction over TA in a cell mixture sample when 50% of the TA present in the cell mixture sample is contributed by the specified cell-type. Higher percentage contribution values can improve the performance of cell-type specific expression determination in cell mixture sample. Therefore, 60%, 70%, 80%, 90% or above can be used as threshold value for criteria in selection of cell-type informative genes.

FIG. 5 is a graph 500 showing the relationship between percentage contribution of a transcript in a cell mixture sample by a specified cell-type subpopulation and folds difference of TA in specified cell-type subpopulation fraction over TA in the cell mixture sample (X) for subpopulations of various proportional cell count from 0.05 (5%) to 0.5 (50%) according to embodiments of the present invention. The horizontal axis 510 is the X-fold difference in expression level of a gene in the specific subpopulation relative to the expression level of the gene in the cell mixture. The vertical axis 520 is the percentage of transcripts that are contributed by a specific subpopulation. The value of 0.5 corresponds to 50% of the cell mixture. Six different lines drawn with different symbols correspond to relationship properties for different subpopulations with different proportional cell counts, not from the same sample though. Each subpopulation has a different proportional cell count P, as shown in the legend 530 with the corresponding symbols. The six separate lines are shown for proportional cell counts (P) of 0.05, 0.1, 0.15, 0.2, 0.3 and 0.5 with the corresponding symbols. For example, line 502 represents the property for a cell type present at a proportional cell count of 0.05 (5%) and line 501 for another one with a proportional cell count of 0.1 (10%). Each line generally follows the form of C % (Y-axis)=X*P.

The dashed lines illustrate the use of FIG. 5 in defining the criteria values of, for example X50, for subpopulations of proportional cell count of 0.1 (10%) and 0.05 (5%) in a cell mixture, and the corresponding X50 values are 5 and 10, respectively. For example, horizontal portion 540 of the dashed line originates from the 0.5 value on the vertical axis and it intersects with line 501 at the point where X (shown on x-axis) is equal to 5. The dashed horizontal line 540 then intersects with line 502 at the point where X is equal to 10. As lines 501 and 502 represent the relationship properties for cell types present at proportional cell count of 0.1 and 0.05, these two values can correspond to the required threshold values of X50s. When higher percentage contribution is desirable, the correspondent values of fold difference X can also be obtained from graph 500. When other percentage contribution is desirable, for example 60%, one can use this graph 500 to calculate the corresponding X60 for different subpopulations present at various proportion cell count values by draw another horizontal dashed line at different level of the vertical axis. For example, X60 for a subpopulation with proportional cell count of 0.05 is 12 and that for another subpopulation with proportional cell count of 0.1 is 6. Since the general formula for the lines is C %=X*P, one can use X=C %/P, where C % is expressed in decimal form. With C %=60% and P=0.1 (line 501), this provides 0.6/0.1, which provides 6 as given in FIG. 6.

C. Expression for Only Two Subpopulations

In some embodiments, the expression level is available only for the specified cell-type fraction and some other cell fractions but not available for the cell mixture sample. The following discussion address methods for using the expression levels of the subpopulations to determine whether a gene satisfies criteria to be an informative gene for a subpopulation.

Figure 6:
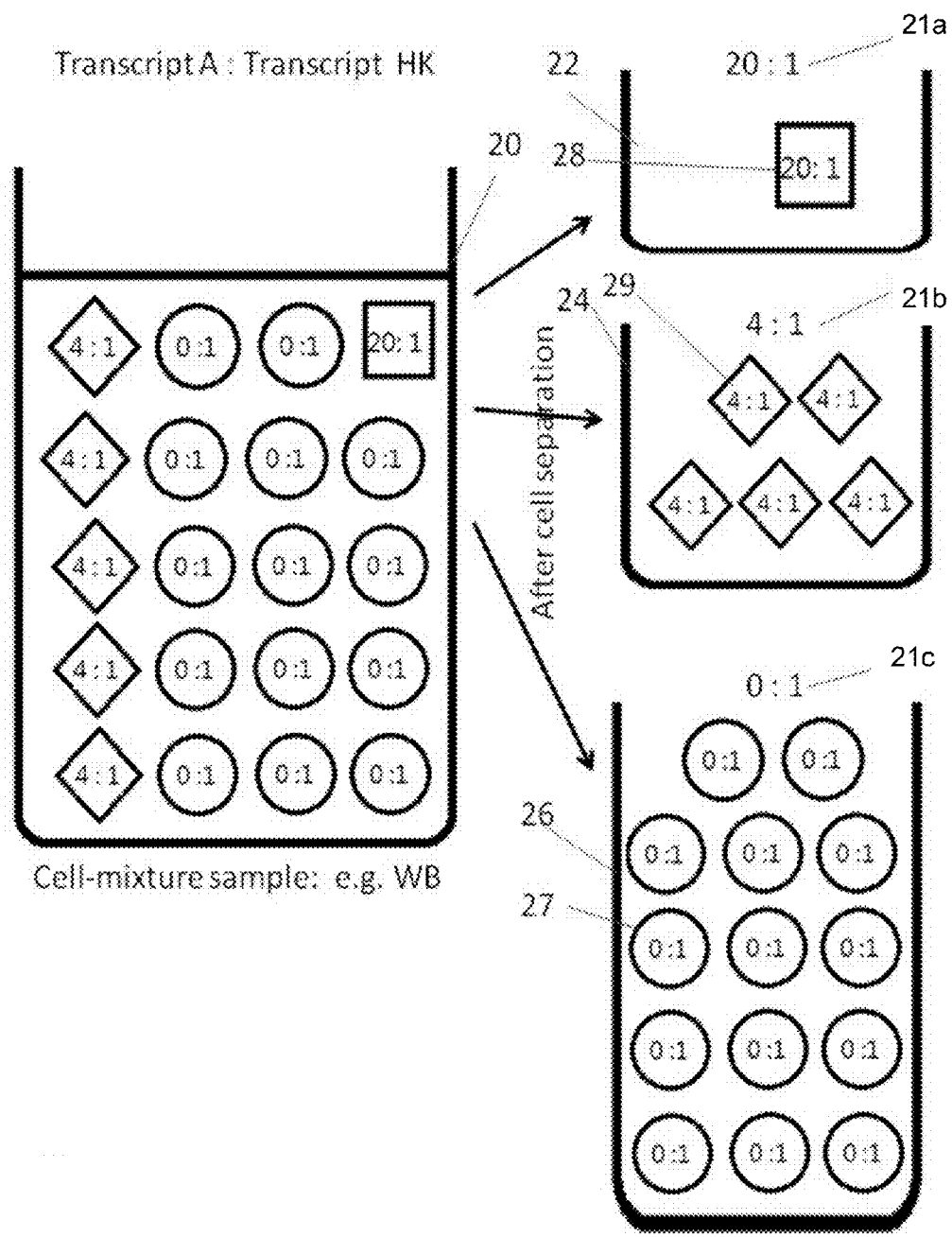
FIG. 6 shows a hypothetical example about a cell-mixture sample to establish properties used for selection of cell-type subpopulation informative genes when gene expression measurements are only available for two subpopulations but not the cell-mixture sample according to embodiments of the present invention.

FIG. 6 shows a scenario when gene expression measurements are only available for two or more subpopulations but not the cell-mixture according to embodiments of the present invention. For example, TA data are only available for cell fraction samples but not the cell mixture sample. This data can still be used to determine a subpopulation informative gene. FIG. 6 is different from FIG. 2 in that relative quantification of gene expression is not performed for the cell-mixture sample 20. Rather, transcript abundance is determined in two or more cell-type fractions after cell separation procedures, and only two of the fractions have any appreciate transcript abundance.

Cell-mixture sample 20 (e.g., peripheral whole blood) has three types of cells, which are represented by different shape including "square" 28, "rhomboid" 29 and "circle" 27. Again the "square" cell 28 is the cell-type subpopulation of interest for which a cell-type informative TA assay is being created. The same threshold criteria for selection of cell-type informative transcript is used, i.e., gene transcript or RNA expressed by the cell-type of interest contributes to at least 50% of transcript of that gene in the cell-mixture sample 20. In the cell-mixture sample 20, 50% of Transcript A is contributed from the "square" cell-type 28. Therefore, Transcript A fulfills the threshold criteria of a cell-type informative transcript for "square" cell-type 28.

The cell-type mixture sample 20 is sorted to yield three purified cell fraction samples 22, 24, and 26 for each of the three cell-types (subpopulations) 27, 28, and 29. A relative quantification of transcript A can be carried out in at least some of these cell fraction samples, which include purified square cell sample 22, purified rhomboid cell sample 24, purified circle cell sample 26. The ratios 21a-c shown inside each cell represent the relative expression of transcript A to transcript HK in a particular subpopulation. These ratios 21a-c are the quantities or expression data that are observed and obtained by experiment for the isolated cell fractions 22-26. As one can see, subpopulation 28 has a ratio of 20:1, subpopulation 29 has a ratio of 4:1, and subpopulation 27 has no appreciable expression of transcript A.

The ratios shows that the relative expression of Transcript A to Transcript HK is 5-fold higher in the purified "square" cell sample 22 over that of "rhomboid" cell sample 24. Under such a condition, a gene with at least a 5-fold higher relative expression difference between two purified cell fractions is useful as subpopulation informative gene, given such proportion cell counts of the two cell fractions (i.e., a 1:5 proportion of cell counts for subpopulation 28 to subpopulation 29) and negligible expression in other cell-types (i.e., subpopulation 27).

The function of cell-type specific relative expression times proportional cell count of the cell-type of interest can serve as a criterion in selection of subpopulation informative genes. In FIG. 6, the value of such function for "square" cell 28 and "rhomboid" cell 29 are 20×5%=1 and 4×25%=1, respectively. One criterion used is that the function value of other cell-type should not exceed that of the cell-type of interest. An upper bound of expression of transcript A in another cell-type (e.g., "rhomboid" cell subpopulation 29) is a function of the ratio of proportional cell counts of the target cell-type (e.g. "square" cell subpopulation 28) and that of the other cell-type expressing the same transcript. This condition is particularly relevant to define subpopulation informative transcripts for CD4 T cells and CD8 T cells.

This threshold ratio as the criteria for selection of subpopulation informative genes is denoted as X50 ("square" cell:"rhomboid" cell). Such threshold ratios X50 ("square" cell:"rhomboid" cell) also applies to data of gene expression obtained by other methods like microarray or sequencing datasets where global normalization of intensity data is performed.

D. General Formulation when Expression for Only Two Subpopulations

In some embodiments, if a gene is only expressed by two subpopulations in a cell mixture sample, it may be desirable to use higher threshold for selection of cell-type or subpopulation informative genes. For example, X75 represents three out of four transcripts of the particular gene being contributed by the specified cell-type of interest, or a signal to noise ratio of three. The following formulae illustrate how to determine the required folds of differential expression between two subpopulations expressing the same gene of interest in the process of defining and selecting subpopulation informative genes.

Let Ep1 be the transcript abundance (TA) of a particular gene in the specified cell subpopulation 1, e.g. CD4 T cell. P1 is the proportional cell count of subpopulation 1 in the cell mixture sample. Ep2 is the transcript abundance of a particular gene in the specified cell subpopulation 2, e.g. CD8 T cell. P2 is the proportional cell count of subpopulation 2 in the cell mixture sample. In this example, X is the fold difference of TA of a gene in a separated fraction of subpopulation 1 compared to that of subpopulation 2, and thus equals Ep1/Ep2. C % is the desirable percentage contribution towards the total amount of transcript in cell-mixture sample by subpopulation 1

The amount of transcript of a gene produced by subpopulation 1 equals Ep1*P1. The amount of Transcript of a gene produced by subpopulation 2 equals Ep2*P2. To determine the value of X for a specific values for the proportional cells counts P1 and P2, and for a desired C %, the following equations can be used:

$$\frac{Ep1*P1}{Ep2*P2} = \frac{C\ \%}{(1-C\ \%)}. \quad (8)$$

Therefore the X value at a given C % can be obtained from the following equation:

$$\frac{Ep1}{Ep2} = \frac{C\ \%}{(1-C\ \%)} * \frac{P2}{P1}. \quad (9)$$

As an example, the typical proportional cell counts of CD4 and CD8 T cells in peripheral blood sample are 20% and 10%, respectively. The required C % is specified for a particular cell-type subpopulation assay (e.g., Direct LS-TA assay). For example, C % can be specified as 75%, such that 75% of the transcript are contributed by the subpopulation 1 as the criterion of subpopulation informative gene. The following criteria can be used to identify subpopulation informative genes for the subpopulations of CD4 and CD8 T cells for C % being 75% (i.e. X75 threshold).

The gene is not expressed by cell types other than CD4 and CD8 at a significant level. Then, for CD4 informative genes, X75 (CD4 to CD8)=0.75/(1−0.75)*0.1/0.2=3*½=1.5. Therefore, genes with differential expression of 1.5 fold higher in the CD4 cell fraction are potentially useful as CD4 informative genes in a peripheral blood Direct LS-TA assay. For CD8 informative gene, X75(CD8 to CD4)=3*2=6. Therefore, genes with differential expression of 6 fold higher in the CD8 cell fraction are potentially useful as CD8 informative genes in a peripheral blood Direct LS-TA assay. It is illustrated by this example that subpopulation specific gene expression in certain cell-types is more readily determined in the cell mixture sample. For example, more subpopulation informative genes are available for the CD4 subpopulation Direct LS-TA assay.

E. Expression Level Available for all Subpopulations

Figure 7:
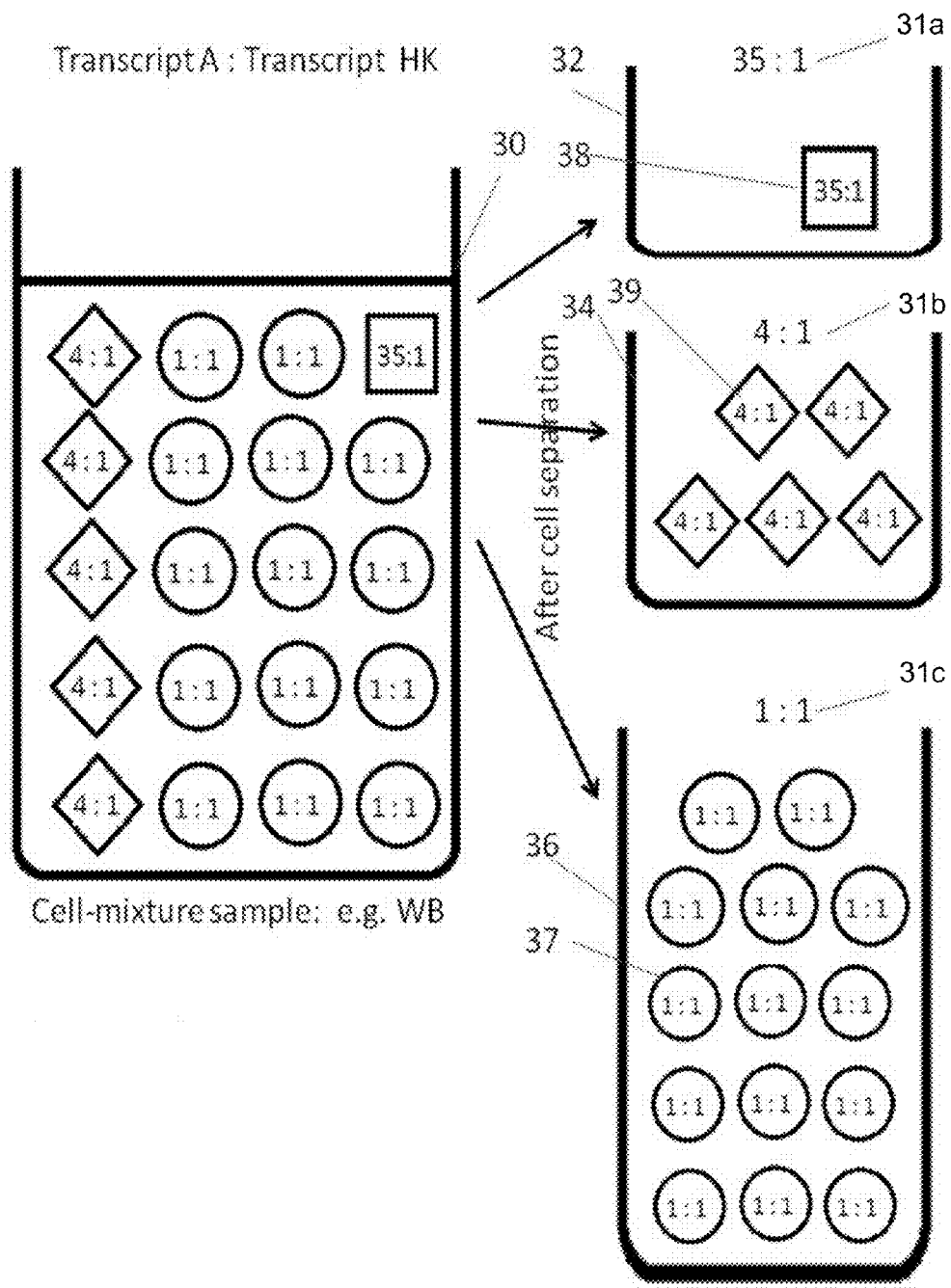
FIG. 7 is another schematic presentation about a cell-mixture sample to establish properties used for selection of cell-type subpopulation informative genes when gene expression measurements are only available for the subpopulations but not the cell-mixture sample according to embodiments of the present invention.

FIG. 7 is another schematic presentation about a cell-mixture sample to establish properties used for selection of cell-type subpopulation informative genes when gene expression measurements are only available for the subpopulations but not the cell-mixture sample according to embodiments of the present invention. This hypothetical situation is similar to FIG. 6, but now the target transcript is expressed by all three cell-types.

Cell-mixture sample 30 (e.g., peripheral whole blood) has three types of cells, which are represented by different shape including "square" 38, "rhomboid" 39 and "circle" 37. Again the "square" cell 38 is the cell-type subpopulation of interest for which a cell-type informative TA assay is being created. In the cell-mixture sample 30, more than 50% of Transcript A is contributed from the "square" cell-type 38. Therefore, Transcript A fulfills the threshold criteria X50 of a cell-type informative transcript for "square" cell-type 38.

Cell-mixture sample 30 can be separated into fractions 32, 34, and 36. The transcript abundance for each fraction, along with the proportional cell count, can be used to determine whether at least 50% of the transcripts for the entire cell-mixture sample come from subpopulation 38. In the present example, it is determined that the ratios 31a-c relative to the HK gene are 35:1 (Ep(1)) for subpopulation 38 (proportional cell count P(1) of 5%), 4:1 (Ep(2)) for subpopulation 39 (proportional cell count P(2) of 25%), and 1:1 (Ep(3)) for subpopulation 37 (proportional cell count P(3) of 70%). To determine whether the X50 criteria is satisfied, Ep(1)*P(1) ≥Ep(2)*P(2)+Ep(3)*P(3), or more generally:

$$EP(1)*P(1) \geq \sum_{i=2}^{N} Ep(i)*P(i). \quad (10)$$

N is an integer corresponding to a number of subpopulation in which the respective gene is expressed. For higher criteria than 50%, the above formula can be modified accordingly. For example, for 75%, a factor of three can be multiplied to the right hand side. Generally for a threshold of C %, a factor of C %/(1−C %) can multiply the right hand side of equation (10).

The examples in FIGS. 3, 6, and 7 can be repeated for more than one sample. An average (or other statistical value) can then be taken over the set of samples. The average can be used to determine whether on average a particular gene is informative. For example, it can be determined whether a subpopulation expresses at least a predetermined percentage of transcripts of a gene over the set of samples.

F. Identifying Reference

The informative reference gene for a subpopulation can be chosen as the informative gene with the lowest biological variation of a set of subpopulation informative genes. The set of subpopulation informative genes does not have to be an exhaustive set of all informative genes for a particular subpopulation. In one embodiment, the biological variation is required to be below a threshold value. The reference gene can be identified by evaluating the biological variation for each of the informative genes in the set, and then selecting the informative gene with the lowest variation (or potentially any reference gene with lower variation than the target gene). More than one informative gene can be used as a reference gene, with the group being effectively considered as a single gene. The TA of the target gene would then be compared to the TA of the group of reference genes to determine the parameter in step 260 of method 200. The TA of the group of reference genes would be increased whenever the transcript of any one of the reference genes is detected. Thus, like the alternative expressions of ddCT, several of the reference genes could be grouped into one normalization factor, for example by taking a geometric mean of TA of multiple reference genes.

G. Identifying Target

Typically, the target gene is one that is known or hoped to be correlated to a particular condition, e.g., a disease state. During initial analysis, the correlation may not be known. But once correlation is known, the identified target gene can be used in a diagnosis. More than one target gene (i.e. a group of target genes) can be used in a similar manner as more than one reference gene can be used.

IV. Calculation of Parameter

The parameter calculated in step 260 can be determined using any mathematical expression of the expression level of the target gene relative to the expression level of the reference gene for the subpopulation. The parameter can be used to assess the expression of the target gene in the particular cell-type subpopulation (e.g. B lymphocytes) based on a correlation of the parameter to an expression level in an isolated fraction of the particular cell-type subpopulation. The parameter can be a summative index, where the TA of multiple reference genes or target genes are combined into a single amount and then used as the first amount or second amount into the mathematical expression used to determine the parameter.

Figure 9:
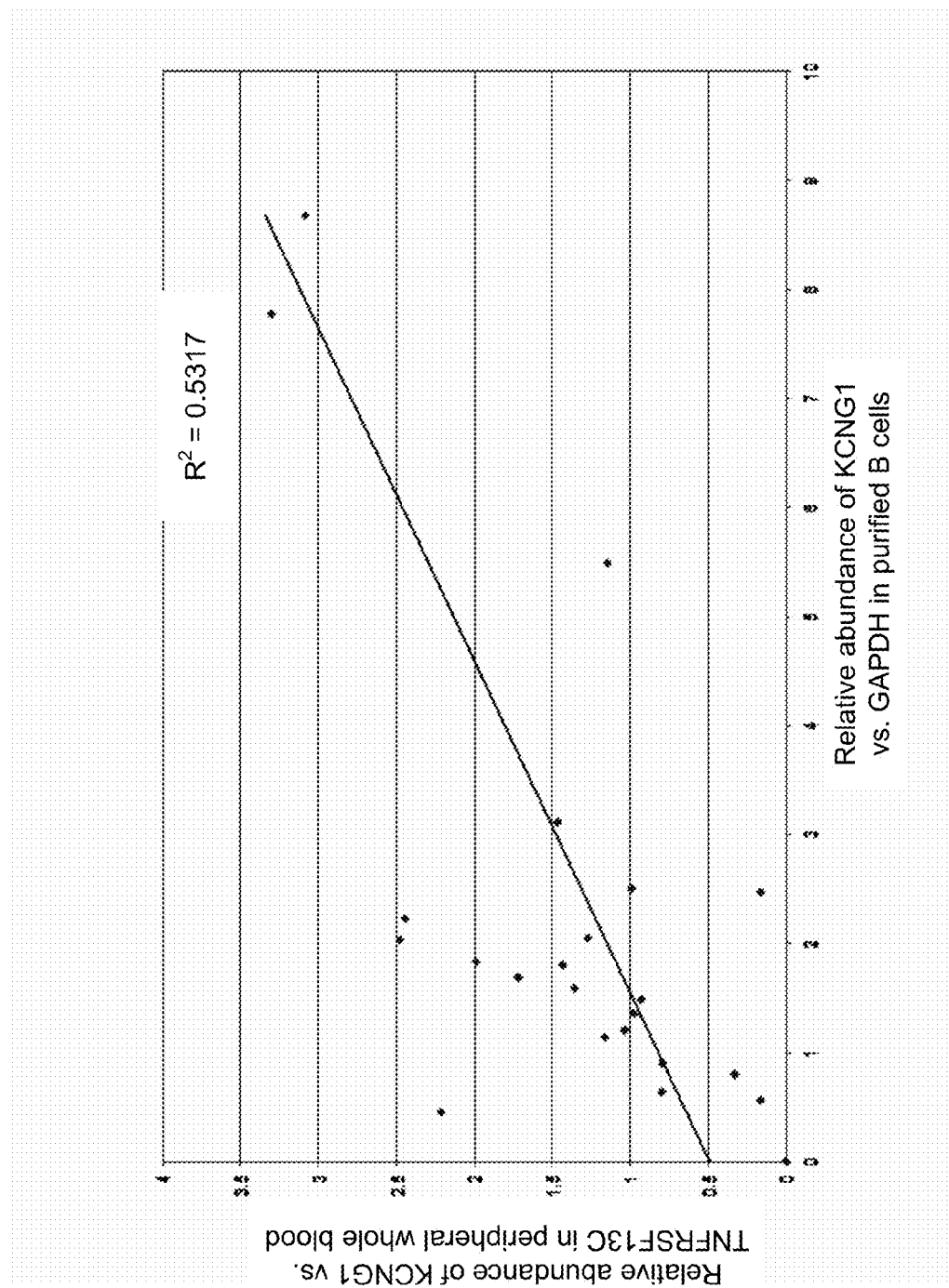
FIG. 9 is a graph showing the correlation between the new method of gene quantification using subpopulation informative genes in a cell mixture sample (y axis, relative expression of KCNG1 vs TNFRSF13C in peripheral whole blood) and the same target gene quantified by gold standard method using conventional housekeeping gene in purified subpopulation (x axis, relative expression of KCNG1 vs GAPDH in purified B cell fraction).

It is demonstrated that this new parameter applied in Direct LS-TA, such as a ratio of transcript abundance of two genes or two sets of genes, when both fulfill the criteria of X(50) or better, correlates significantly to the transcript abundance of the target genes in the specific leukocyte subpopulation after purification. FIG. 9 discussed later shows an example of such correlation. Therefore, embodiments herein can determine a leukocyte subpopulation specific gene expression without the need to enrich or purify for the leukocyte subpopulation of interest.

Embodiments can also involve quantification of transcript abundance of at least two genes (including the cell-type informative target gene and another cell-type informative reference gene) or two sets of such genes for relative expression of a target gene of interest. Quantification of the two genes or two sets of genes can be carried out in cell mixture samples, like peripheral whole blood sample. The two genes or two sets of genes can be selected in such a way that they fulfill the criteria of X50 or better.

The parameter can be compared to one or more cutoff values to determine a classification of the cell mixture. The cutoff values can be determined from samples of individuals known to be healthy or otherwise normal. The classifications can include whether the cell mixture is in a diseased state or a non-diseased state. For example, a range of values below a cutoff can be associated with a disease state, and a range of values above the cutoff can be associated with a non-diseased state, or vice versa.

V-1. Example 1 (B Lymphocytes)

The following examples are provided by way of illustration only and not by way of limitation. Those of skill in the art will readily recognize a variety of non-critical parameters that could be changed or modified to yield essentially the same or similar results.

A. Preparation

Blood samples were collected from 22 healthy volunteers. All samples were processed to collect B lymophocytes by magnetic bead cell separation. Quantification of candidate references genes were carried out in (1) Peripheral whole blood treated with Tizol, (2) peripheral blood collected in PAX tubes, (3) PBMC collected by Ficoll preparation and (4) the purified B lymphocytes by 2 steps reverse transcription real-time PCR.

Although both red blood cells and platelets are not nucleated cell, both contains gene transcripts. However, both of them only contain transcripts of much smaller number of genes than nucleated hematopoietic subpopulations, which is the leukocyte subpopulations. In one embodiment, one may filter out genes and transcripts expressed by non-nucleated cell populations in peripheral blood. Such a step still leaves a cell-mixture of different subpopulations. This filtering may be done particularly when both cell-type informative target genes and cell-type informative reference genes are also expressed at high levels in red blood cells or platelets. The subpopulation target gene and the subpopulation reference gene can be chosen so as not to have appreciable expression levels in red blood cells or platelets.

B. Identification of Genes with Selected Differential Expression Value (X)

Quantification of conventional housekeeping genes were carried out in each sample preparation. Quantification of the candidate leukocyte subpopulation informative reference genes were carried out in each sample preparation. Relative abundance in all samples were determined by ΔΔCT (delta-delta threshold cycle) method.

Gene expression analysis was performed using pairs of exon-spanning primers. Reverse transcription was performed with Roche Transcriptor First Strand cDNA kit (Roche). Real time quantitative PCR was performed with Roche 480 machine. Delta-delta threshold cycle (ΔΔCT) method was used to determine the target gene expression of a test sample relative to a standard sample. The standard sample was a pooled sample of whole blood samples extracted from two volunteers. Therefore, this ΔΔCT was used to calculate the folds difference of expression of a target gene in the B cell fraction over that in the whole blood. GAPDH was used as the universal housekeeping gene in the conventional way for the analysis of TA for the purified B cells.

The following genes in Table I were analyzed by QPCR to identify informative genes for the B cell subpopulation.

TABLE I

List of genes with ID, primer, and product size.

| Gene | RefSeq ID | primers (SEQ ID NO:) | product size |
|---|---|---|---|
| APOBEC3F | NM_145298 | AATTATGCATTCCTGCACCG(1) CCATAGGCTTTGCGTAGGTT(2) | 110 |
| DCAL1 | NM_172004 | AAAACTGTTCGGACTTCCCC(3) ATGCACCTTCCAGTCTTTGG(4) | 111 |
| FREB | NM_032738 | TACCTTTCCCTTGGTGTGCT(5) CAGCTGCTCTCCTCAGTGC(6) | 101 |
| GAPDH | NM_002046 | CAATGACCCCTTCATTGACC(7) GACAAGCTTCCCGTTCTCAG(8) | 106 |
| KCNG1 | NM_002237 | ACCTCTCCGTCAGCACCTT(9) AGGAGGAACTCCAGGGAGAA(10) | 127 |
| KLHL14 | NM_020805 | CTCCCCAGCAATTTGGTTC(11) AGTTTTCCACCTCCACAACG(12) | 109 |
| LAF4 | NM_002285 | CCAAGCTCTCCAAGTTCAGC(13) ACTTTGCCAGGTGCTTGAAT(14) | 136 |
| Prickle1 | NM_001144881 | TGCAGAACTGCTCAAACCAC(15) GTTTCACACTCAAGGCAGCA(16) | 120 |
| SNX22 | NM_024798 | GCTTGGAGGCTTACATCCAG(17) AGTTGCTAGCCTTGGGGTCT(18) | 111 |
| TNFRSF13C | NM_052945 | GTGGGTCTGGTGAGCTGG(19) GATTCCCGGAGACAGAATGA(20) | 126 |

The differential expression of candidate B cell subpopulation informative genes in separated B cells sample was compared to the average expression in whole blood sample, as shown in table 800 of FIG. 8A. As the standard samples used in calculation of ddCT in this example was a pooled sample of whole blood from two individuals. The conventional ddCT (target gene vs GAPDH) observed in purified B cells samples represented the extent of differential expression in term of folds. In one embodiment such as this example, it can be a convenient way to determine the extent of differential expression. Therefore, the units for the mean and standard deviation (St. Dev.) are in units of fold over whole blood sample. CV % refers to the coefficient of variation among samples. The results of the test against two criteria X50 and X80 are shown. Note that the Yes or No is dependent on the population cell count for the B cells in the mixture. For both KLHL14 and TNFRSF13C, the upper bound of 95% confident interval of mean folds difference over whole blood reached the criteria of X50, therefore, they were also used.

Gene transcripts that account for 50% of transcripts in average peripheral whole blood samples (i.e. achieving X50 criteria which requires 10 folds higher expression in the B cell fraction sample) include KCNG1, KLHL14, Prickle and TNFRSF13C. There are two genes that achieve X80 criteria: DLCAL1 and FREB. X80 indicates that 80% transcripts in an average peripheral whole blood sample are attributed to those expressed by the B cell subpopulation; a fold difference of at least 16 time higher expression in the B cell fraction is required. These X50 and X80 criteria are based on the average percentage of 5% of B lymphocytes in peripheral whole blood sample. These gene transcripts are expressed in lower levels in other leukocyte subpopulations, including CD4 T cells, CD8 T cells, and granulocytes. Therefore they are specifically informative for the B cell subpopulation.

C. Selecting Reference Gene

Embodiments can use a new way to express the subpopulation specific expression level in a cell mixture sample. Instead of using conventionally defined universal housekeeping gene(s) as internal reference in the quantitative determination of transcript abundances of target gene(s), a new class of internal reference gene(s) is/are used. They are called subpopulation informative reference genes here, such as B lymphocyte informative reference gene.

For example, a leukocyte subpopulation informative reference genes can be selected from a candidate list of informative genes based on a low level of between-sample variance of its relative abundance of transcripts in the subpopulation, e.g., in the B lymphocyte samples. This leukocyte subpopulation informative reference gene is then useful as a reference for another target gene in the cell mixture (whole blood) sample to determine leukocyte subpopulation specific expression of the target gene.

These subpopulation (e.g., leukocyte) reference genes can fulfill two criteria: (1) expression criteria in the subpopulation, e.g., X50 or higher criteria, as described above; (2) low biological variation or variance among various subjects (e.g., different humans). In the example of developing a B lymphocyte subpopulation specific gene expression method, FIG. 8B shows a table 850 of genes (as determined from table 800 of FIG. 8A) that fulfill the criteria for X50 or better: KCNG1, KLHL14, Prickle, TNFRSF13C, DLCAL1 and FREB.

Table 850 shows the CV % (biological variation) of subpopulation informative genes arranged in ascending order from left to right. Conventional gene expression as ΔΔCT using GAPDH as universal housekeeping gene are shown. TNFRSF13C had the least biological variation. Therefore, it is selected as the subpopulation reference gene in an example that follows. KLHL14 and FREB are also potential internal reference genes for other applications. In other situation, a summative index of more than one cell-type informative or leukocyte subpopulation reference genes can also be used as internal reference. There are various ways and formulae to express multiple reference genes in the application of relative gene expression analysis (Vandesompele et al. (2009) Chapter 4. Reference gene validation software for improved normalization. In Real-Time PCR: Current Technology and Applications. Editors Julie Logan, Kirstin Edwards, Nick Saunders. Publisher: Caister Academic Press; 1 edition).

D. Quantification of Target Gene

The subpopulation informative target gene and subpopulation informative reference gene can be used to directly determine leukocyte subpopulation specific expression in peripheral whole blood samples. Quantification of a target gene by its relative abundance against a leukocyte subpopulation informative reference gene by ΔΔCT method in whole blood (cell mixture) samples reflect or correlate to the relative abundance of this target gene against a conventional housekeeping gene determined by ΔΔCT method in a purified B cell samples. Thus, by using a suitable target gene, and a suitable cell-type informative reference gene, it is feasible to determine a relative abundance of the target gene in a single leukocyte subpopulation of whole blood (cell mixture sample) without the requirement of prior cell separation.

In this example, KCNG1 was chosen as the subpopulation target gene. Therefore, the expression level of KCNG1 in B lymphocytes of peripheral blood is of interest. The conventional method using purification is compared to the approach of directly measuring the relative abundance of the subpopulation target gene and reference gene in the cell mixture. The new relative gene expression parameter is obtained by gene expression analysis directly carried out in the peripheral whole blood sample. Same primers are used as shown above. Real time quantitative PCR was performed with Roche 480 machine. Delta-delta threshold cycle (ΔΔCT) method was used as the new parameter of gene expression levels or TA of subpopulation informative target gene, KCNG1 relative to subpopulation informative reference gene, TNFRSF13C.

FIG. 9 is graph 900 showing the correlation between this new parameter of Direct LS-TA, ΔΔCT (specifically relative abundance of KCNG1 in peripheral whole blood sample relative to TNFRSF13C in peripheral whole blood sample) and conventional LS-TA ΔΔCT (KCNG1 in purified B cell subpopulation relative to GAPDH in purified B cell subpopulation). Along the horizontal axis, the relative expression of target gene (KCNG1) was expressed relative to the housekeeping gene in the purified B cell fraction. The relative expression of the target gene (KCNG1 using GAPDH as internal reference in purified B cell samples obtained from 22 volunteers) is taken as the gold standard for determining the accuracy of the new Direct LS-TA parameter.

The coefficient of determination ($R^2$) is over 0.5 ($p<0.01$). In some embodiments, a value of 0.5 can be used as a threshold to determine whether a particular Direct LS-TA assay provides sufficient accuracy for testing the expression of subpopulation target genes in a subpopulation. In other embodiments, the performance of a Direct LS-TA assay could be evaluate by statistical significance of correlation coefficient (r). Graph 900 shows a linear relationship between ΔΔCT(KCNG1/TNFRSF13C in peripheral whole blood sample) and ΔΔCT(KCNG1/GAPDH in purified B cell subpopulation). As a result of this correlation, embodiments can determine gene expression of selected target genes in leukocyte subpopulation sample by direct analysis of gene expression in cell mixture samples of peripheral whole blood.

This example uses gene expression in B lymphocytes in peripheral blood, which accounts for 5% of cellular component in peripheral whole blood (WB) sample. Therefore this approach is shown to work for a leukocyte subpopulation that represents around 5% of all leukocytes in peripheral whole blood sample. As the results show a significant correlation between direct-LS transcript abundance assay (Y-axis) and gene expression in separated cell by conventional cell sorting (X-axis), it is demonstrated that an assessment of expression of KCNG1gene of B lymphocyte could be achieved without prior separation of B lymphocytes. Embodiments described here are also applicable to other cell mixture sample types including but not limited to tissue biopsy of solid organs.

More examples of application of whole blood Direct LS-TA assays to determine gene expression levels in hematological subpopulations are included below. Table II, III, IV, and V provide a list of candidate subpopulation informative genes that could be used in whole blood Direct LS-TA assays according to various subpopulation of interest.

V-2. Example 2 (Total T Lymphocytes)

Regarding methods and subjects, blood samples of thirty consented healthy individuals were included in this example. Two types of samples were used, which were (1) peripheral whole blood immediately treated with Trizol reagent (Invitrogen, US) after collection and (2) CD3 total T cells separated (or enriched) samples from each individuals. For isolation of CD3+ve total T cells subpopulation, PBMC was prepared from freshly collected whole blood samples. Then CD3 micro beads (Miltenyi Biotec) was added. After incubation as instructed by the manufacturer's protocol, the mixture was then washed and passed through a magnetic field in a LS column (Miltenyi Biotec). After further rounds of washing inside the column, the enriched/purified samples of the CD3+ve T cells subpopulation were harvested by elution after removal of the magnetic field. An aliquot of the enriched sample was analysed by two-color immunofluorescence flow cytometry to confirm enrichment of CD3+ve T cells. The remaining portion was treated by Trizol reagent and stored at −80° C. Using this method of magnetic sorting, the percentage of CD3+ve T cells were over 80% in the subpopulation enriched samples.

TA of the following candidate genes were examined by real-time QPCR after reverse transcription. The general laboratory procedures described in the sections of Example 1 (B lymphocytes) and section VI. Laboratory Procedures were followed. Instead of using a pooled whole blood sample processed by Trizol reagent as standard sample for calculation of ddCT as in the case of Example 1 (B lymphocytes), another type of blood sample was used. The differential expression of enriched T cells cannot be directly revealed by ddCT values of the enriched T cell samples. Therefore, the differential expression over whole blood samples was determined individually for each participant as a ratio of the ddCT value of the enriched cell sample to ddCT value of the whole blood sample. Then summary statistics (mean and standard deviation) were calculated from these ratios.

Four conventional house-keeping genes (ACTB, GAPDH, RPS18, RPL31) were analyzed by QPCR, their results were summarized by taking a geometric mean of the 4 delta-CT values (GeoMean). The delta-CT (dCT) value of a gene was calculated by the PCR efficiency corrected method using the difference of CT values of a test sample and the control sample.

To identify subpopulation informative genes for CD3+ve T lymphocyte subpopulation, the ratios of TA (expressed as ddCT of candidate gene vs Geometric means of 4 House-keeping genes) of candidate genes in the CD3+ve T cells enriched sample to TA of those genes in the corresponding whole blood sample from the same individual was calculated. These relative expression ratios (X, folds) of candidate CD3+ve T cell subpopulation informative genes are shown in table 1000 of FIG. 10A. All candidate gene except PRKCQ fulfilled the X50 criteria which required a 2-fold higher expression in T cell subpopulation then in whole blood. The biological variance in the enriched samples of CD+ve T cell subpopulations is shown in table 1050 of FIG. 10B. And GIMAP7 had a low variance and was used as a subpopulation reference gene.

Whole blood Direct LS-TA assays for these 7 genes (except PRKCQ, which failed X50 criteria and GIMAP7, which was used as subpopulation reference gene) were performed. Correlations between results from whole blood Direct LS-TA assays and the corresponding gene expression level (TA) in separated CD3+ve T cells were determined. Cell type specific expression of 5 genes had a strong positive correlation with the results by whole blood Direct LS-TA assays with coefficients of determination ($R^2$) greater than 0.5, representing correlation coefficients (r) of greater than 0.7. The correlations between Direct LS-TA assays and gene expression determined after subpopulation separation (gold standard method) are shown in table 1060 of FIG. 10C.

Figure 11A:
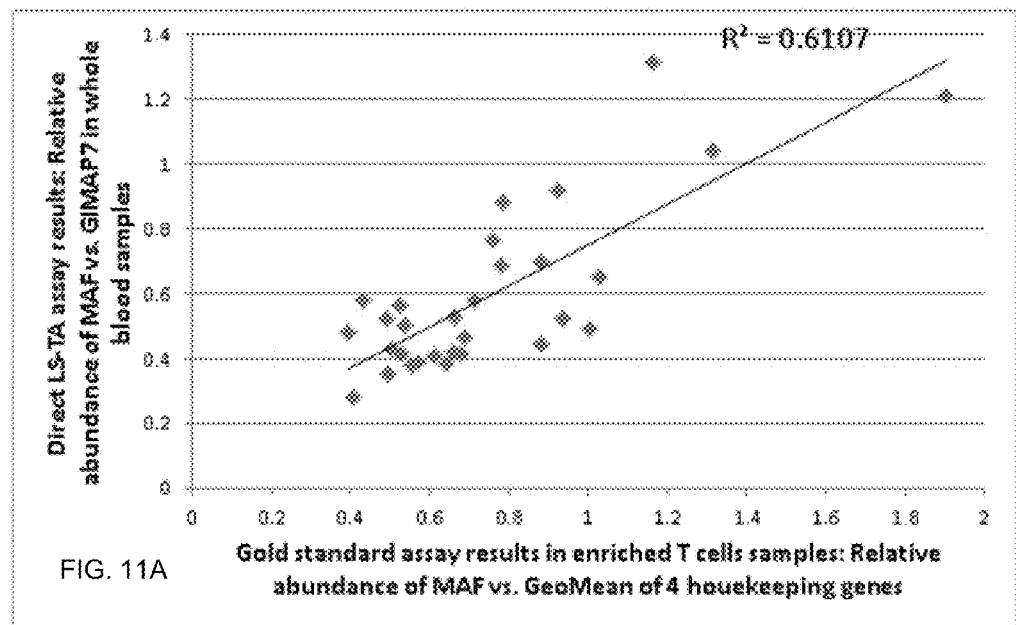
FIG. 11A is a graph showing the correlation between the Direct LS-TA assay of MAF (y axis) and the same gene quantified by gold standard method using enriched total T cells samples (x axis).
Figure 11B:
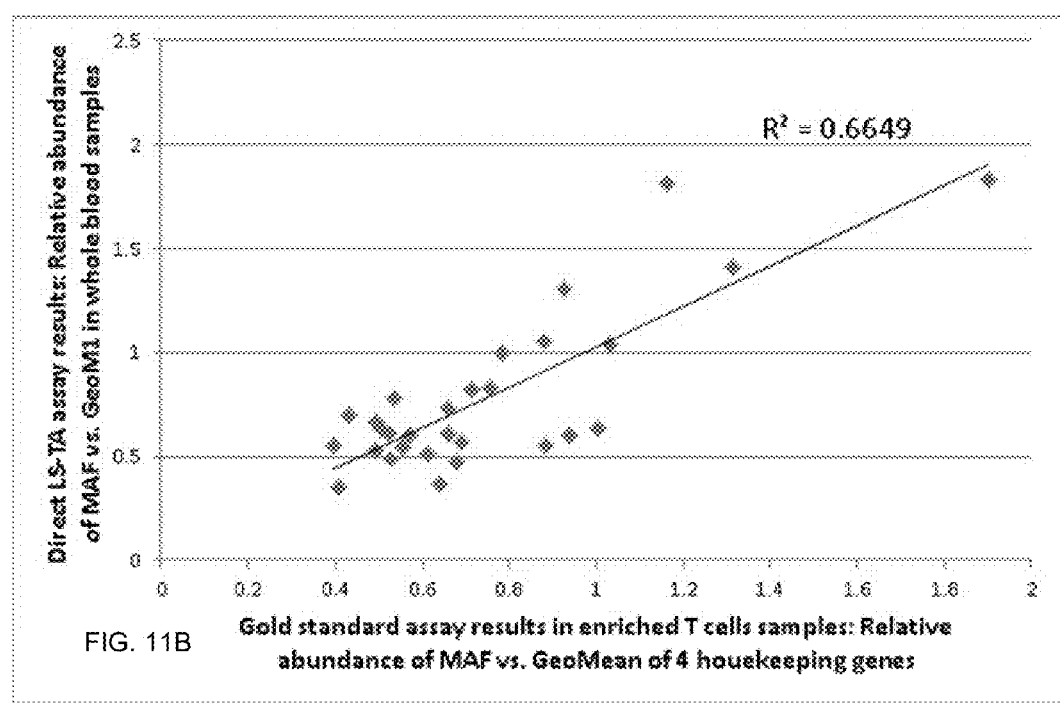
FIG. 11B is a graph showing the performance of Direct LS-TA assay of MAF using two subpopulation reference genes. The correlation coefficients are statistically significant ($p<0.01$).

The correlation between whole blood Direct LS-TA assays and the corresponding gene expression level (TA) in separated CD3+ve T cells are shown in FIGS. 11A and 11B. FIG. 11A shows the results of correlation between whole Blood Direct LS-TA assay for MAF gene using GIMAP7 as subpopulation reference gene and expression level of MAF in separated CD3+ve T cells. A strong correlation between the two assays is shown, $R^2=0.61$.

Two or more subpopulation reference genes could be used at the same time in the whole Blood Direct LS-TA assay. In this example, a geometric mean (GeoM1) of dCT values of GIMAP7 and LRRN3 was calculated. Then the relative abundance of MAF was determined based on this value. FIG. 11B shows the results the correlation with gold standard assay results. An improvement in coefficient of determination ($R^2$) was obtained, now 0.6649.

V-3. Example 3 (Granulocytes)

Regarding methods and subjects, blood samples of eighty consented healthy individuals were included in this example. In this example, two types of samples were used, which were (1) peripheral whole blood immediately treated with Trizol reagent (Invitrogen, US) after collection and (2) granulocytes separated (or enriched) samples from each individuals. Granulocyte subpopulation was separated from other nucleated cells by Ficoll solution following standard protocol. Granulocytes were collected from the Ficoll-RBC interface after standing in room temperature and centrifugation. After rounds of washing, the enriched/purified samples of granulocytes subpopulation were collected as pellet after centrifugation and treated by Trizol reagent and stored at −80° C.

TA of the following candidate genes were examined by real-time QPCR after reverse transcription: AQP1, BCL2A1, CEACAM6, CEACAM8, C1orf24, CSF2, DEFA4, FCGR3B, IL-4, IL-8, IL8RB, LTF, MMP25, MS4A3, RNASE3, SOD2. The general laboratory procedures described in the sections of Example 1 (B lymphocytes) and Laboratory Procedures were followed. Four conventional house-keeping genes (ACTB, GAPDH, RPS18, RPL31) were analyzed by QPCR, their results were summarized by taking a geometric mean of the 4 delta-CT values (GeoMean) in conventional TA assays for whole blood and separated granulocyte samples.

To identify subpopulation informative genes for granulocytes subpopulation, the ratios of TA (expressed as ddCT of candidate gene vs GeoMean of 4 Housekeeping genes) of candidate genes in the granulocytes enriched sample to TA of those genes in the corresponding whole blood sample from the same individual were calculated. These relative expressions (X, folds) of candidate granulocytes subpopulation informative genes are shown in table 1200 of FIG. 12A. All candidate genes fulfilled the X50 criteria which required that TA of subpopulation genes in the separated granulocyte samples was equal or higher than TA in whole blood. The biological variance in the enriched samples of granulocytes subpopulations is shown in table 1250 of FIG. 12B. And AQP1 and SOD had a low variance and were used as a subpopulation reference gene.

Figure 13:
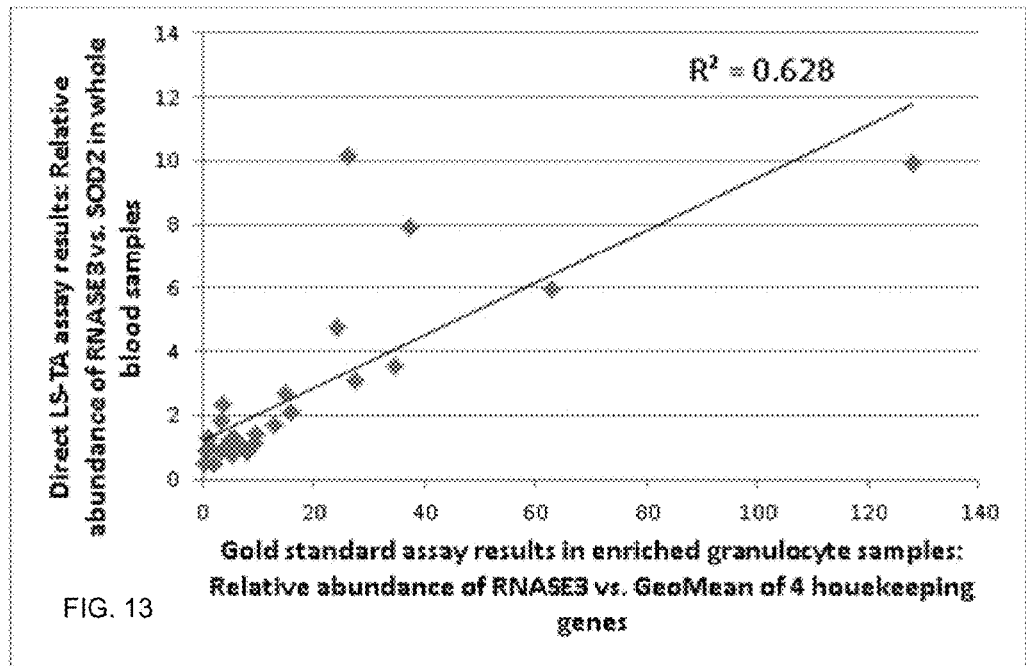
FIG. 13 is a graph showing the correlation between the Direct LS-TA assay of RNASE3 (y axis) and the same gene quantified by gold standard method using enriched granulocyte samples (x axis). The correlation coefficient is statistically significant ($p<0.01$).

Whole blood Direct LS-TA assays for these genes (except AQP1 and SOD2, as they were used as subpopulation reference gene) were performed. Correlations between results from Whole blood Direct LS-TA assays and the corresponding gene expression level (TA) in separated granulocytes were determined. Cell type specific expression of 5 genes had a strong positive correlation with the results by Whole blood Direct LS-TA assays with coefficients of determination ($R^2$) greater than 0.5, representing correlation coefficients (r) of greater than 0.7. The degree of correlations is shown in table 1260 of FIG. 12C. These 4 genes can be assayed by Direct LS-TA method, which are CEACAM6, CEACAM8, CSF2, IL8, and RNASE3. FIG. 13 is a graph showing the correlation between the Direct LS-TA assay of RNASE3 (y axis) and the same gene quantified by gold standard method using purified the granulocyte samples (x axis).

V-4. Example 4 (Microarray Data)

In the above example of whole blood Direct LS-TA for total T lymphocytes, GIMAP7 and LRRN3 were used as subpopulation reference gene for measurement of gene expression of CD3+ve total T cells. It was validated by real-time QPCR assay. For example, using real-time QPCR, TA of a target gene in a specific subpopulation of a cell-mixture sample can be determined by a ratio of dCT of that subpopulation target gene to dCT of a subpopulation reference gene. This present example is an embodiment in which microarray data can be used in a Direct LS-TA assay.

Data of gene expression measured by microarray platforms are commonly expressed as signal intensities and it is common practice to present the results after log transformation. Direct LS-TA assays in the context of microarray data is an extension of the same principle with a log transformation. After log transformation, log (signal intensity of target gene in the separated subpopulation) can be related to [log(signal intensity of subpopulation target gene in cell mixture sample)–log(signal intensity of a subpopulation reference gene in cell mixture sample)].

In the example of whole blood Direct LS-TA for total T lymphocytes, GIMAP7 and LRRN3 have been shown to be accurate subpopulation reference genes. Here, a microarray dataset was used to demonstrate the application and performance of Direct LS-TA with microarray data. Laudanski et al studied gene expression by microarray in 3 types of hematological samples including a cell mixture sample (total leukocytes) and 2 subpopulation samples (enriched T cells and enriched monocytes). The dataset is available at Gene Expression Omnibus by accession GSE5580. (Laudanski, et al. 2006. "Cell-specific Expression and Pathway Analyses Reveal Alterations in Trauma-related Human T Cell and Monocyte Pathways." Proceedings of the National Academy of Sciences of the United States of America 103 (42)

(October 17): 15564-15569.) These samples were collected from 7 control subjects and 7 patients and blood samples from each individual were processed to the three cell types or cell mixtures for microarray analysis. After normalization of microarray data, signal intensity data were log transformed. Data of these genes studied in the example of T cell subpopulation were retrieved and analyzed, including BCL11B, ITK, PRKCQ, GIMAP7, CD3G, GZMK, MAF, NELL2, and LRRN3. However, GIMAP7 was not qualified by that microarray platform. Therefore, LRRN3 was used as subpopulation reference gene.

Figure 14A:
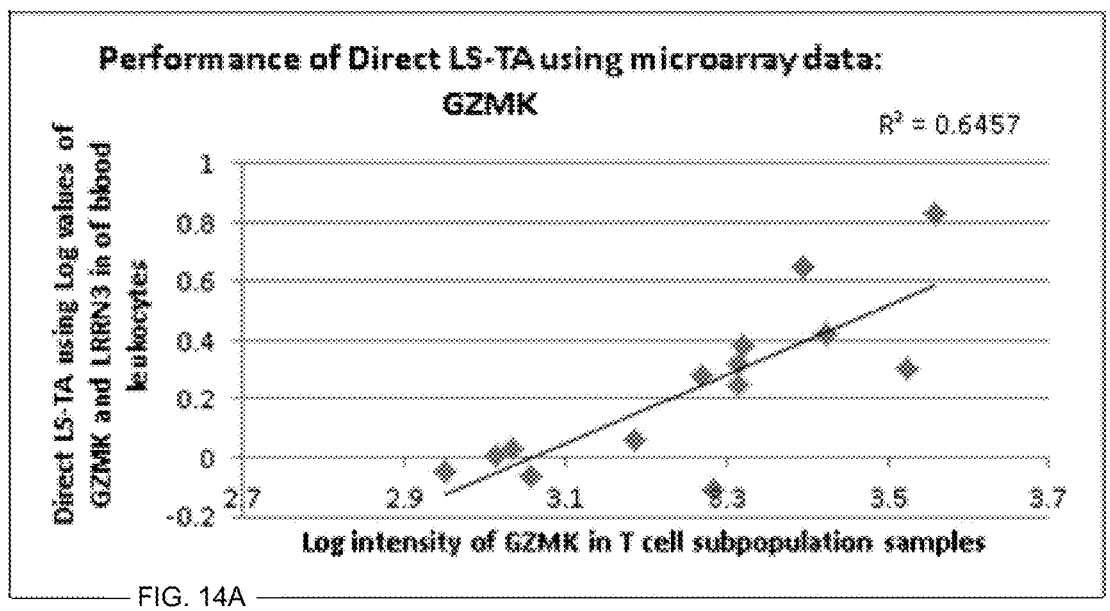
FIG. 14A is a graph showing the performance of Direct LS-TA assay using microarray data for GZMK gene.
Figure 14B:
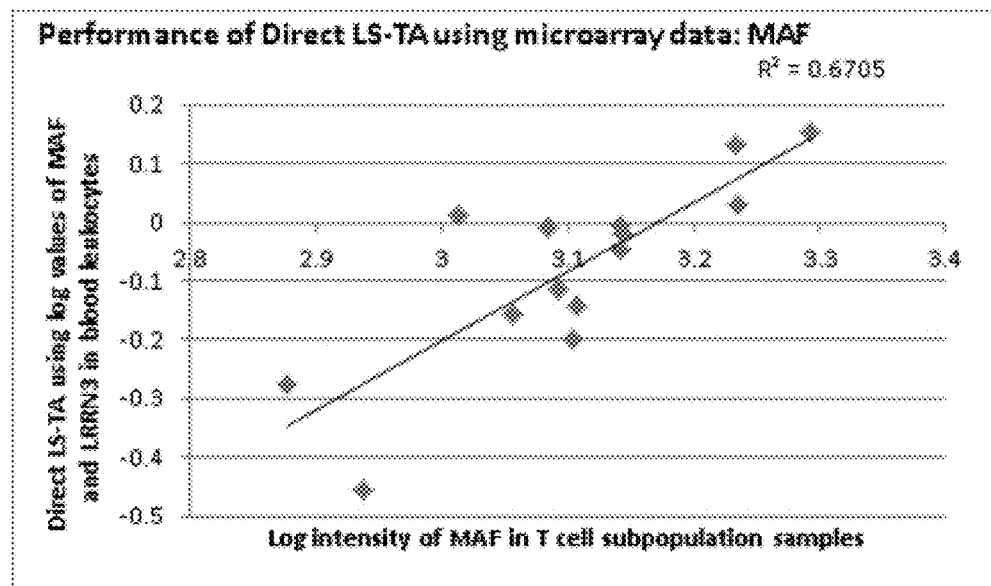
FIG. 14B is a graph showing the performance of Direct LS-TA assay using microarray data for MAF gene.
Figure 14C:
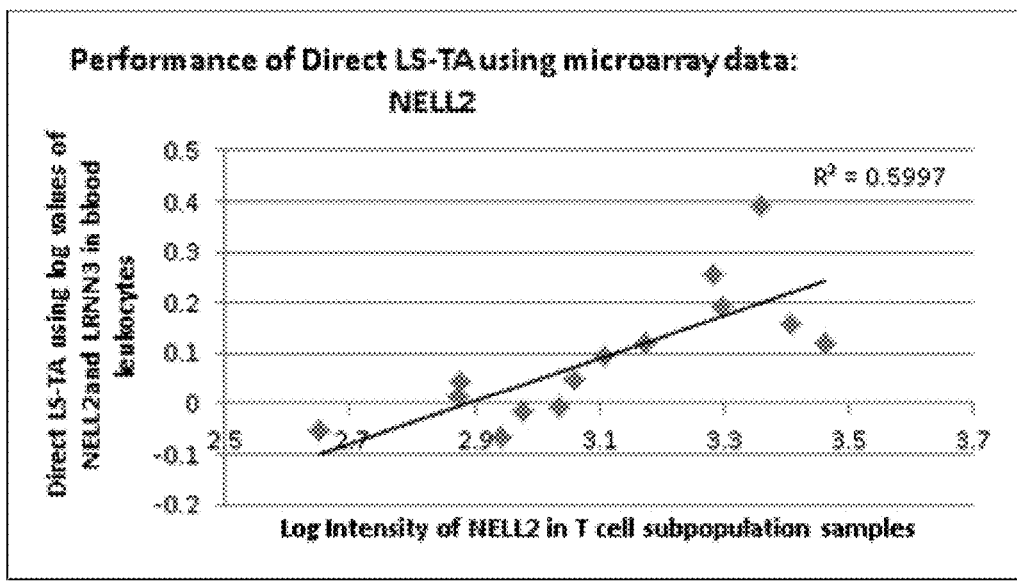
FIG. 14C is a graph showing the performance of Direct LS-TA assay using microarray data for NELL2 gene. All correlation coefficients are statistically significant ($p<0.01$).

The performance of Direct LS-TA with these microarray data is shown in FIGS. 14A-14C. In FIG. 14A, Direct LS-TA for GZMK gene was calculated as the difference between log of signal intensity of GZMK (206666_at) and LRRN3 (taken as the mean of 2 probes: 209840_s_at and 209841_s_at). The results strongly correlated ($R^2=0.65$) with expression in separated T cell samples, shown on the x-axis in FIG. 14A. The performance of both Direct LS-TA assays for MAF (206363_at) and NELL2 (206666_at) genes were also comparable, as shown in FIGS. 14B and 14C. These results demonstrated the readily extension of Direct LS-TA to microarray data. And it is also equally applicable to transcriptome data generated by sequencing methods, like RNA-seq using massive parallel sequencing technologies.

VI. Laboratory Procedures

Below are some laboratory procedures used in the above examples. These procedures are implementations that may be used in various embodiments and are not restrictive as to other procedures that may be used.

For the preparation of a PBMC sample, the blood sample was mixed with equal volume of PBS buffer, and then it was gently added above 3 ml Ficoll-Paque plus (GE Health, Cat. No. 17-1440-02). The tube was centrifuged at 500×g for 25 min without brake. The (PBMC) middle layer was collected to a new 15 ml tube and wash with PBS for two times. Then it was centrifuged at 100×g for 10 min. The PBMC pellet at the bottom of the tube was transferred to a 2 ml microcentrifuge tube with 750 ul Trizol LS reagent (Invitrogen, Cat. No. 10296-028).

For separation of CD4/CD8/CD14/CD19 subpopulation fraction samples, 50 ul CD4/CD8/CD14/CD19 micro beads (Miltenyi Biotec, Cat. No. 130-045-101/130-045-201/130-050-201/130-050-301) were added to PBMC sample prepared as described above. The tube was mixed well and incubated in 2-8° C. with shaking for 15 min. After incubation, cells were washed by adding 10 ml wash buffer (PBS+1% FBS) and centrifuge at 445×g for 10 min at room temperature. After removal of supernatant, wash buffer was added to total volume of 3 ml to resuspend the cells. LS column was placed (Miltenyi Biotec, Cat. No. 130-042-401) in the magnetic field of a suitable MACS separator, and it was first balanced with 3 ml separation buffer (Miltenyi Biotec, Cat. No. 130-091-221). The cell suspension was then passed through the balanced LS column. The column was washed by 3 ml separation buffer three times. The specified subpopulation was harvested by removing the LS column from the magnetic separator and elution with 5 ml separation buffer using the plunger. A cell pellet was obtained by centrifuge at 500×g for 5 min which was resuspended and treated with Trizol LS reagent, and stored at −80° C. until analysis.

For collection of peripheral blood into PAXgene tubes, 3 ml whole blood was collected from the volunteers and stored in PAXgene Blood RNA Tube (QIAGEN, Cat. No. 762165). They were stored at −80° C. until analysis.

For Trizol-treated whole blood samples, an aliquot of 300 ul whole blood sample was mixed directly with 900 ul Trizol LS reagent. It was stored at −80° C. until analysis.

For Trizol treated RNA sample extraction, RNA extraction was performed using QIAGEN RNeasy Mini Kit (Cat. No. 74106). After the sample was homogenized and incubated samples at room temperature, 60 ul BCP was added per 500 ul volume of Trizol sample. After shaking and standing at room temperature for 2-3 min, it was centrifuged at 12,000×g, 4° C. for 5 min. The upper aqueous phase was transferred to a new tube, then 300 ul 100% isopropanol was added and mixed well immediately by pipetting. Up to 700 ul of this mixture was added to an RNeasy mini column placed within a 2 ml collection tube. Repeat applying the sample after flow-through until all sample was loaded to the column. QIAGEN RNase-Free DNase Set (Cat. No. 79254) was used for DNase treatment. To elute, two rounds of 40 ul and 30 ul pre-warmed RNase-free water was used. RNA concentration was measured using Nanodrop system. RNA integrity was checked by gel. RNA samples were either reverse transcribed or stored the well-labeled samples in −80° C. freezer for future use.

For RNA extraction from PAXgene blood sample, RNA extraction from PAXgene blood RNA tube (QIAGEN, Cat. No. 762165) was performed using QIAGEN PAXgene blood RNA kit (Cat. No. 762174). Standard protocol provided by the kit was followed. RNA concentration was measured using Nanodrop system. RNA integrity was checked by gel. RNA samples were either reverse transcribed or stored the well-labeled samples in −80° C. freezer for future use.

For reverse transcription, the reverse transcription was conducted using Roche Applied Science Applied Science Transcriptor First Strand cDNA Synthesis kit (Cat No. 04897030001). In preparation step, up to 1 ug extracted total RNA was mixed together with 2.5 uM Oligo(dT), 60 uM random primer and 10 ug/ml MS2 RNA (Roche Applied Sciencec Applied Science, Cat No. 10165948001). After keeping at 65° C. for 10 min, 4 ul Transcriptor RT reaction buffer (5×), 1 mM of each dNTP, 0.5 ul of each of Protector RNase inhibitor (final concentration of 20 U) and Transcriptor Reverse Transcriptase (final concentration of 10 U) were added. Then it was kept at 25° C. for 10 min, followed by 30 min at 55° C. for cDNA synthesis. Finally, the Transcriptor Reverse Transcriptase was inactivated by heating to 85° C. for 5 min. Some examples used Takara PrimeScript® RT reagent Kit (Perfect Real Time) (Cat No. HRR037C, Takara, Janpan) in a reaction mixture with 2 ul 5× PrimeScript® buffer, 0.5 ul Oligo dT Primer (final concentration of 25 pmol), 0.5 ul Random Primer (final concentration of 50 pmol) and 0.5 ul PrimeScript® RT Enzyme. Then 6.5 ul total RNA was added and incubated at 37° C. for 10 min to synthesis cDNA, and then followed inactivation step. After reverse transcription, cDNA was stored at −80° C.

In one embodiment, a two-step reverse transcription quantitative PCR (rt-QPCR) approach is used. One-step rt-QPCR can also be used. Multiple hematopoietic subpopulation informative reference genes may be used, as in other setup of rt-QPCR using conventional housekeeping reference genes. (Logan et al. 2009. Real-Time PCR: Current Technology and Applications (Book), Publisher: Caister Academic Press. Publication date: January 2009. ISBN: 978-1-904455-39-4). Other analysis methods are also applicable, such as analysis of variance (Tichopad et al. 2009. Design and optimization of reverse-transcription quantitative PCR experiments. Clin Chem. 55 (10): 1816-23).

In the application of real-time quantitative PCR, measurement of gene expression (transcript abundance) is commonly expressed as a ratio of the expression levels of the target gene (gene of interest) to a house-keeping gene. House-keeping genes are those genes that are expressed universally by various tissues or cells at a stable level.

In the application of real-time quantitative PCR, measurement of gene expression (transcript abundance) can be classified into either (1) absolute quantification or (2) relative quantification. With calibration standards of given concentration of gene transcripts (for example, number of copies per unit volume), it is possible to determine the number of copy of a transcripts present in a sample by comparing the results between the test sample and calibrator. On the other hand, relative quantification is more commonly used. The level of expression (or TA) of a gene of interest, also known as the target gene, is expressed in relative term (as a ratio) to level of expression (TA) of one or more House-keeping gene (HK gene). In order to correct for difference in PCR efficiency between amplification protocols for target gene and HK gene, a method called delta-delta CT (ddCT) is used. In delta-delta CT method, the threshold cycle values of the test samples obtained by real-time PCR were compared against a control sample which data is common to all test samples. Therefore, the delta-delta CT results reflect the relative level of expression of the target gene against that in the control sample. Delta CT (dCT) refer to the difference of threshold cycle values of one gene between a test sample and the control sample.

For real-time QPCR, gene expression was quantified by Real-time PCR use Roche Applied Sciencec Applied Science real-time PCR system. Lightcycler 480 SYBR Green I Master Mix kit (Roche Applied Sciencec Applied Science, Cat. No. 04887352001) was used. Total volume of each reaction was 10 ul, including 5 ul 2× Master Mix, 0.5 ul of each primer (10 uM) and 4 ul cDNA template (10-folder diluted after reverse transcription step). In some examples, Takara SYBR Premix Ex Taq™ (Tli RNase H) kit (Cat No. HRR420D, Takara, Japan) was used. The PCR master mixture contained 5 ul 2× Premix Ex Taq™ (Tli RNase H), 0.2 ul of each of primers (final concentration of 0.2 uM), 2 ul cDNA and 2.6 ul ddH$_2$O to make 10 ul working volume. All QPCR reactions were prepared on robotic stations, Biomek® 2000 and Biomek® NX robotic system (Beckman Coulter, Fullerton, Calif., USA). Real-time PCR was run on Roche Light cycler 480 instrument with system related software (Light Cycler® 480 software, v1.5). Standard protocol of amplification was performed by initially heating the reaction mixture at 95° C. for 5 min, followed by the cycle of denaturation for 10 sec at 95° C., 10 sec at 60° C. for annealing, and 10 sec at 72° C. for extension, which repeated for 45 times. After the thermocycling step, a melting program was performed to check for any non-specific product. A series of serially diluted cDNA samples were use as standard control with the gradient from 4-folder dilution to 256-folder dilution. In addition, 10-folder diluted positive control and non-template RT negative control were also included in Real-time PCR. All reactions were done in duplicate.

Although the examples were carried out using quantitative real time PCR. Any other methods of quantitative measurement of RNA or DNA molecule can be used. Besides using comparative threshold method (ΔΔCT, or ddCT) with efficiency correction to interpret the threshold cycle value (CT), other methods can also be used, including but not limited to, absolute standard curve method and relative standard curve method (Pfaffl, M W. 2001. "A new mathematical model for relative quantification in real-time RT-PCR." *Nucleic Acids Research* 29 (9) (May 1): e45) and Pfaffl et al. 2002. "Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the bovine species." *Domestic Animal Endocrinology* 22 (2) (April): 91-102).

VII. List of Informative Genes

A. Data-Mining of Publicly Available Data to Identify Subpopulation Informative Genes An additional approach to identify subpopulation informative genes is data-mining publicly available microarray dataset. Few datasets have quantified whole blood sample and hematopoietic subpopulation fraction in the sample experiment. One example is Julià et al 2009. "Identification of candidate genes for rituximab response in rheumatoid arthritis patients by microarray expression profiling in blood cells." *Pharmacogenomics* 10 (10) (October): 1697-1708. doi:10.2217/pgs. 09.99. It is available in NCBI GEO at www.be-md.ncbi.nlm.nih.gov/projects/geo/query/acc.cgi?acc=GSE15316.

The same criteria is used as above in selection of B cell subpopulation informative genes which is X50 (B cell to whole blood). It requires that the candidate gene is expressed in B cell fraction at a level 10 times of that in the whole blood sample, since the proportional cell count is 5%. Table II below provides a list of the B cell subpopulation informative genes that were identified.

TABLE II

Candidate B lymphocyte subpopulation informative genes

| Microarray probe identifier | gene symbol | Nucleotide sequence in NCBI database |
|---|---|---|
| GI_10835070-S | CD74 | NM_004355.1 |
| GI_11038671-A | CD79A | NM_021601.1 |
| GI_1038675-A | CD79B | NM_021602.1 |
| GI_11415027-S | TCL1A | NM_021966.1 |
| GI_13904868-S | RPS29 | NM_001032.2 |
| GI_14916502-A | RPS24 | NM_001026.2 |
| GI_5431308-S | RPS7 | NM_001011.2 |
| GI_15812219-S | RPL31 | NM_000993.2 |
| GI_17017970-S | RPL26 | NM_000987.2 |
| GI_18641371-S | HLA-DRB3 | NM_022555.3 |
| GI_18641372-S | HLA-DRB4 | NM_021983.3 |
| GI_18641377-S | HLA-DOB | NM_002120.2 |
| GI_21071007-S | TCN1 | NM_001062.2 |
| GI_23110953-S | CTSG | NM_001911.2 |
| GI_23110986-A | MS4A1 | NM_021950.2 |
| GI_23110992-S | MS4A3 | NM_006138.3 |
| GI_23238191-S | TNFRSF17 | NM_001192.2 |
| GI_24797068-S | HLA-DQB1 | NM_002123.2 |
| GI_26665892-S | HLA-DRB5 | NM_002125.3 |
| GI_28178862-S | OSM | NM_020530.3 |
| GI_28416954-S | AZU1 | NM_001700.3 |
| GI_31317226-S | EGR1 | NM_001964.2 |
| GI_31317229-S | FCER1A | NM_002001.2 |
| GI_31542945-S | CXXC5 | NM_016463.5 |
| GI_31982886-S | GATA2 | NM_032638.3 |
| GI_32189367-S | IGJ | NM_144646.2 |
| GI_32481214-S | CD19 | NM_001770.3 |
| GI_32484980-S | BANK1 | NM_017935.2 |
| GI_33469981-S | BLK | NM_001715.2 |
| GI_34147598-S | FCER2 | NM_002002.3 |
| GI_38455401-S | LCN2 | NM_005564.2 |
| GI_39753969-S | CAMP | NM_004345.3 |
| GI_39930348-S | KIAA0746 | NM_015187.1 |
| GI_41197088-S | HLA-DQA1 | XM_371812.1 |
| GI_42544162-S | FREB | NM_032738.3 |
| GI_42794770-A | TXNDC5 | NM_030810.2 |
| GI_4502446-S | BPI | NM_001725.1 |
| GI_4502650-S | CD22 | NM_001771.1 |
| GI_4502662-S | CD37 | NM_001774.1 |

TABLE II-continued

Candidate B lymphocyte subpopulation informative genes

| Microarray probe identifier | gene symbol | Nucleotide sequence in NCBI database |
|---|---|---|
| GI_4503302-S | DEFA4 | NM_001925.1 |
| GI_4503548-S | ELA2 | NM_001972.1 |
| GI_4507176-S | SPIB | NM_003121.1 |

B. List for X75 with E-TABM-633 Dataset

Data-mining was also performed of publicly available gene expression dataset in which various hematopoietic cell subpopulations had been analysed by microarray (Watkins et al. 2009 "A HaemAtlas: characterizing gene expression in differentiated human blood cells." *Blood* 113 (19) (May 7): e1-9). The dataset is available at www.bi.ac.uk/arrayexpress/experiments/E-TABM-633.

For selection of CD4 T cell subpopulation informative genes in the setting of direct LS-TA analysis of peripheral whole blood sample, X75 (CD4 cell to CD8 cell) was used which indicated that CD4 subpopulation informative genes needed a 1.5 fold higher expression in CD4 T cells than CD8 T cells. After filtering for genes that were not expressed by granulocytes, which was defined as having ⅛ or ¹⁄₁₆ of that in T cells, table III shows the list of candidate CD4 T cell subpopulation informative genes. As with other tables of informative genes, the target gene and reference gene can be selected from such a list for the given subpopulation.

TABLE III

Candidate CD4 subpopulation informative genes identified by X75 criteria as obtained by data-mining of E-TABM-633 dataset.

| Gene symbol | Nucleotide sequence in NCBI database |
|---|---|
| ABLIM1 | NM_006720.3 |
| BCL2 | NM_000633.2 |
| CCR7 | NM_001838.2 |
| CD5 | NM_014207.2 |
| HS.13262 | Hs.13262 |
| HS.567464 | Hs.567464 |
| HS.579530 | Hs.579530 |
| LDHB | NM_002300.3 |
| LEF1 | NM_016269.2 |
| LOC388344 | XM_371023.4 |
| MAF | NM_005360.3 |
| MYC | NM_002467.3 |
| PIK3IP1 | NM_052880.3 |
| PRKCA | NM_002737.2 |
| TNFRSF7 | NM_001242.3 |
| TRAT1 | NM_016388.2 |

For identifying CD8 subpopulation informative gene, X66 (CD8 to CD4) was used as the criteria. These genes have 4-fold higher expression in CD8 than CD4 cells. After filtering for genes that were not expressed by granulocytes, which was defined as having ⅛ of that in T cells, and excluding those expressed at a two-fold higher level by NK cells than CD8 Tcells, table IV shows the list of CD8 T cell subpopulation informative genes.

TABLE IV

Candidate CD8 subpopulation informative genes identified by X66 criteria as obtained by data-mining of E-TABM-633 dataset.

| Gene symbol | Nucleotide sequence in NCBI database |
|---|---|
| NKG7 | NM_005601.3 |
| DUSP2 | NM_004418.2 |
| KLRK1 | NM_007360.1 |
| GZMH | NM_033423.2 |
| NCR3 | NM_147130.1 |
| CD8A | NM_001768.4 |
| EOMES | NM_005442.2 |
| CCL5 | NM_002985.2 |
| CTSW | NM_001335.2 |

C. List for X50 with E-TABM-633 Dataset

For granulocytes (or even for the more specific neutrophils), as it is the most prevalent cell type in peripheral blood, X50 (granulocyte to another subpopulation) could be met with a 0.1-fold difference in expression level of a gene in a subpopulation relative to the cell mixture when the proportional cell count of granulocytes is 50% and the other subpopulation is 5%. There are more than 1000 genes showing a 2-fold higher expression in granulocytes than other hematopoietic subpopulations. Only the top 150 candidate granulocyte subpopulation informative genes are shown in the following table. Many genes coding for various ribosomal proteins in this table are promising candidate granulocyte subpopulation informative reference genes.

TABLE V

Top 150 candidate granulocyte subpopulation informative genes identified data-mining of E-TABM-633 dataset

| Gene symbol | Nucleotide sequence in NCBI database |
|---|---|
| CLC | NM_001828.4 |
| FCGR3B | NM_000570.2 |
| ALPL | NM_000478.2 |
| MMP9 | NM_004994.2 |
| PGLYRP1 | NM_005091.1 |
| MME | NM_007288.1 |
| CCR3 | NM_178329.1 |
| CMTM2 | NM_144673.2 |
| IL8RA | NM_000634.2 |
| MMP25 | NM_022718.2 |
| CYP4F3 | NM_000896.1 |
| PBEF1 | NM_005746.1 |
| S100P | NM_005980.2 |
| CAMP | NM_004345.3 |
| IL8RB | NM_001557.2 |
| PRSS33 | NM_152891.1 |
| TNFAIP6 | NM_007115.2 |
| TFF3 | NM_003226.2 |
| SLPI | NM_003064.2 |
| DEFA3 | NM_005217.2 |
| OLIG2 | NM_005806.2 |
| DEFA1 | NM_004084.2 |
| NOV | NM_002514.2 |
| FFAR2 | NM_005306.1 |
| IL5RA | NM_175728.1 |
| ANXA3 | NM_005139.1 |
| SLC25A37 | NM_016612.1 |
| PROK2 | NM_021935.2 |
| IL8 | NM_000584.2 |
| CA4 | NM_000717.2 |
| LRG1 | NM_052972.2 |
| TCN1 | NM_001062.2 |
| LOC653600 | XM_928349.1 |
| KRT23 | NM_015515.3 |
| PANX2 | NM_052839.2 |
| PBEF1 | NM_182790.1 |

TABLE V-continued

Top 150 candidate granulocyte subpopulation informative genes identified data-mining of E-TABM-633 dataset

| Gene symbol | Nucleotide sequence in NCBI database |
|---|---|
| GPR97 | NM_170776.3 |
| IL1R2 | NM_173343.1 |
| MXD1 | NM_002357.2 |
| KCNJ15 | NM_002243.3 |
| CEACAM8 | NM_001816.2 |
| TGM3 | NM_003245.2 |
| KCNJ2 | NM_000891.2 |
| GPR109B | NM_006018.1 |
| ALOX15 | XM_937556.1 |
| IFIT2 | NM_001547.3 |
| GPR109A | NM_177551.3 |
| LOC653117 | XM_931656.1 |
| VNN3 | NM_001024460.1 |
| LCN2 | NM_005564.2 |
| ORM1 | NM_000607.1 |
| CCL23 | NM_005064.3 |
| CEACAM3 | NM_001815.1 |
| INDO | NM_002164.3 |
| CEBPE | NM_001805.2 |
| FBXL13 | NM_145032.2 |
| ADM | NM_001124.1 |
| DEFA4 | NM_001925.1 |
| C3ORF34 | NM_032898.2 |
| CACNG6 | NM_031897.2 |
| ROPN1L | NM_031916.2 |
| PSG11 | NM_002785.2 |
| HIST1H2BE | NM_003523.2 |
| HIST1H2BC | NM_003526.2 |
| C1ORF24 | NM_022083.1 |
| CEACAM1 | NM_001024912.1 |
| ZDHHC18 | NM_032283.1 |
| REPS2 | XM_942570.1 |
| GPR44 | NM_004778.1 |
| IL1R2 | NM_004633.3 |
| FPR2 | NM_001462.3 |
| RNASE3 | NM_002935.2 |
| CEACAM6 | NM_002483.3 |
| SLC45A4 | XM_944850.1 |
| AQP9 | NM_020980.2 |
| LOC654103 | XM_939368.1 |
| ARG1 | NM_000045.2 |
| HS.193406 | Hs.193406 |
| EPHB1 | NM_004441.3 |
| PHOSPHO1 | NM_178500.2 |
| LOC653778 | XM_929667.1 |
| HS.524705 | Hs.524705 |
| IFIT3 | NM_001549.2 |
| MANSC1 | NM_018050.2 |
| C1ORF24 | NM_052966.1 |
| RNF24 | NM_007219.2 |
| REPS2 | NM_004726.1 |
| MGAM | NM_004668.1 |
| GPR97 | XM_936582.1 |
| GNG10 | NM_001017998.1 |
| SOD2 | NM_001024465.1 |
| LTF | NM_002343.2 |
| STX3 | NM_004177.3 |
| EMR3 | NM_032571.2 |
| NRBF2 | NM_030759.1 |
| HCG27 | NM_181717.1 |
| OR10G3 | NM_001005465.1 |
| IL1B | NM_000576.2 |
| ALOX15 | NM_001140.3 |
| HS.482814 | Hs.482814 |
| MBOAT7 | NM_024298.2 |
| PSG9 | NM_002784.2 |
| LOC283547 | XM_378454.3 |
| CEACAM1 | NM_001712.3 |
| HS.131087 | Hs.131087 |
| HS.282800 | Hs.282800 |
| TNFRSF10C | NM_003841.2 |
| PTGS2 | NM_000963.1 |
| IL1RAP | NM_002182.2 |
| LOC642112 | XM_936252.1 |
| LOC651738 | XM_944898.1 |
| ACSL1 | NM_001995.2 |
| LOC552891 | NM_004125.2 |
| TRIB1 | NM_025195.2 |
| ADORA3 | NM_000677.2 |
| DGAT2 | NM_032564.2 |
| HSPA6 | NM_002155.3 |
| LOC643313 | XM_933030.1 |
| FRAT2 | NM_012083.2 |
| FAM174A | NM_198507.1 |
| HS.569349 | Hs.569349 |
| ASPRV1 | NM_152792.1 |
| OXER1 | NM_148962.3 |
| HS.576627 | Hs.576627 |
| HS.540131 | Hs.540131 |
| XPO6 | NM_015171.1 |
| RNF149 | NM_173647.2 |
| VNN2 | NM_004665.2 |
| MAK | NM_005906.3 |
| IFRD1 | NM_001550.2 |
| LOC642684 | XM_926137.1 |
| SLC2A11 | NM_001024938.1 |
| LOC653503 | XM_929619.1 |
| VNN3 | NM_078625.2 |
| LOC651612 | XM_940794.1 |
| HECW2 | NM_020760.1 |
| SMPD3 | NM_018667.2 |
| LOC649154 | XM_938223.1 |
| STEAP4 | NM_024636.1 |
| HS.161796 | Hs.161796 |
| ABTB1 | NM_172027.1 |
| F2RL1 | NM_005242.3 |
| KIAA1324 | NM_020775.2 |
| DHRS9 | NM_005771.3 |
| TMEM154 | NM_152680.1 |
| ORF1-FL49 | NM_032412.2 |
| DPEP3 | NM_022357.1 |
| CXCL1 | NM_001511.1 |
| C19ORF22 | NM_138774.2 |
| TMCC3 | NM_020698.1 |

D. List of X50 with GSE5580 Dataset

For identification of subpopulation informative genes for CD3+ve total T cells, the X50 (T cell to whole blood) is 2. It requires that candidate subpopulation genes are expressed two times higher in total T cells fraction than in whole blood. Dataset of microarray expression by Laudanski et al had data on total leukocyte sample (as an alternative of whole blood sample) and enriched total T cell samples from patients and controls. It is available at www.ncbi.nlm.nih.gov/geo/query/acc.cgi?acc=GSE5580. There are more than 250 genes fulfilling this criteria as candidate total T cell subpopulation genes. Only the top 75 genes are listed here.

TABLE VI

Candidate CD3+ve total T cell subpopulation informative genes identified by X50 criteria by data-mining of GSE5580 dataset.

| Probe ID | Gene Symbol | Nucleotide sequence in NCBI database |
|---|---|---|
| 209795_at | CD69 | NM_001781 |
| 205590_at | RASGRP1 | NM_005739 |
| 208798_x_at | GOLGA8A | NM_015003 |
| 204891_s_at | LCK | NM_005356 |
| 205798_at | IL7R | NM_002185 |
| 203828_s_at | IL32 | NM_004221 |
| 204777_s_at | MAL | NM_002371 |
| 213539_at | CD3D | NM_000732 |

TABLE VI-continued

Candidate CD3+ve total T cell subpopulation informative genes identified by X50 criteria by data-mining of GSE5580 dataset.

| Probe ID | Gene Symbol | Nucleotide sequence in NCBI database |
|---|---|---|
| 211796_s_at | TRBC1 /// TRBC2 | NG_001333 |
| 210972_x_at | TRAC /// TRAJ17 /// TRAV20 | |
| 206337_at | CCR7 | NM_001838 |
| 210915_x_at | TRBC1 | NG_001333 |
| 201656_at | ITGA6 | NM_000210 |
| 211675_s_at | MDFIC | |
| 202207_at | ARL4C | NM_005737 |
| 202524_s_at | SPOCK2 | NM_014767 |
| 212400_at | FAM102A | |
| 221558_s_at | LEF1 | NM_016269 |
| 213958_at | CD6 | NM_006725 |
| 217838_s_at | EVL | NM_016337 |
| 39248_at | AQP3 | NM_004925 |
| 221756_at | PIK3IP1 | NM_052880 |
| 201697_s_at | DNMT1 | NM_001379 |
| 206150_at | CD27 | NM_001242 |
| 211623_s_at | FBL | NM_001436 |
| 204960_at | PTPRCAP | NM_005608 |
| 200953_s_at | CCND2 | NM_001759 |
| 213649_at | SRSF7 | NM_006276 |
| 218764_at | PRKCH | NM_006255 |
| 212414_s_at | GLYR1 /// SEPT6 | NM_015129 |
| 201030_x_at | LDHB | NM_002300 |
| 217871_s_at | MIF | NM_002415 |
| 217950_at | NOSIP | NM_015953 |
| 205133_s_at | HSPE1 | NM_002157 |
| 201892_s_at | IMPDH2 | NM_000884 |
| 212995_x_at | MZT2B | |
| 200826_at | SNRPD2 | NM_004597 |
| 209440_at | PRPS1 | NM_002764 |
| 214439_x_at | BIN1 | NM_004305 |
| 215091_s_at | GTF3A | NM_002097 |
| 203385_at | DGKA | NM_001345 |
| 202144_s_at | ADSL | NM_000026 |
| 221691_x_at | NPM1 | NM_002520 |
| 201922_at | NSA2 | NM_014886 |
| 200705_s_at | EEF1B2 | NM_001959 |
| 200642_at | SOD1 | NM_000454 |
| 203408_at | SATB1 | NM_002971 |
| 212071_s_at | SPTBN1 | NM_003128 |
| 217848_s_at | PPA1 | NM_021129 |
| 221488_s_at | CUT A | NM_015921 |
| 217802_s_at | NUCKS1 | NM_022731 |
| 205255_x_at | TCF7 | NM_003202 |
| 217807_s_at | GLTSCR2 | NM_015710 |
| 214280_x_at | HNRNPA1 | NM_002136 |
| 207721_x_at | HINT1 | NM_005340 |
| 56197_at | PLSCR3 | NM_020360 |
| 200943_at | HMGN1 | NM_004965 |
| 217969_at | C11orf2 | NM_013265 |
| 201177_s_at | UBA2 | NM_005499 |
| 207023_x_at | KRT10 | NM_000421 |
| 209104_s_at | NHP2 | NM_017838 |
| 201092_at | RBBP7 | NM_002893 |
| 200064_at | HSP90AB1 | NM_007355 |
| 210027_s_at | APEX1 | NM_001641 |
| 201947_s_at | CCT2 | NM_006431 |
| 212426_s_at | YWHAQ | NM_006826 |
| 201812_s_at | C4orf46 /// TOMM7 | NM_019059 |
| 208697_s_at | EIF3E | NM_001568 |
| 216570_x_at | LOC100510735 /// RPL29 | |
| 218495_at | UXT | NM_004182 |
| 200610_s_at | NCL | NM_005381 |
| 200982_s_at | ANXA6 | NM_001155 |
| 211937_at | EIF4B | NM_001417 |
| 209503_s_at | PSMC5 | NM_002805 |
| 201064_s_at | PABPC4 | NM_003819 |

VIII. Kits

Embodiments can provide compositions and kits for practicing the methods described herein to assess the genomic expression of a subpopulation target gene in a first subpopulation of cells of a cell mixture containing a plurality of subpopulations. The genomic expression can be represented by a parameter than be used as a biomarker. For example, the parameter can be compared to one or more cutoffs to obtain a classification for diagnosis or prognosis, e.g., a classification of disease or non-disease.

Kits for carrying out assays for determining genomic expression of a target gene in a first subpopulation of cells of a cell mixture containing a plurality of subpopulations typically include at least one oligonucleotide useful for specific hybridization with the subpopulation target gene (and transcripts thereof) and at least one oligonucleotide useful for specific hybridization with the subpopulation reference gene (and transcripts thereof). Optionally, this oligonucleotide is labeled with a detectable moiety.

In some cases, the kits may include at least two oligonucleotide primers that can be used in the amplification of at least a section of the subpopulation target gene and the subpopulation reference gene. Instead of or in addition to primers, a kit can include a first labeled probe for detecting a transcript of the subpopulation target gene and a second labeled probe for detecting at least a section of a transcript of the subpopulation reference gene.

Typically, the kits also provide instruction manuals to guide users in analyzing test samples and assessing the state of liver physiology or pathology in a test subject.

IX. Computer System

Figure 15:
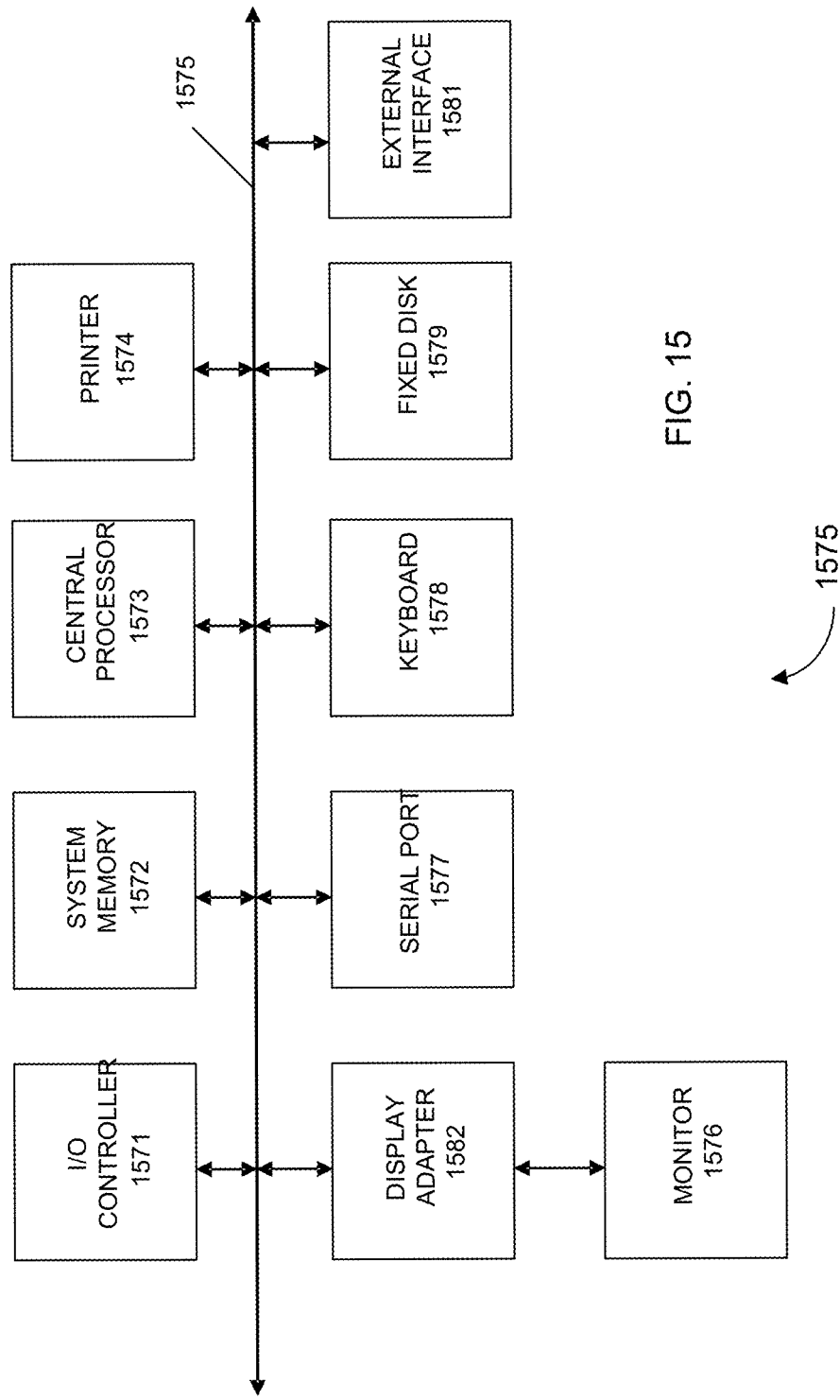
FIG. 15 shows a block diagram of an example computer system 1500 usable with system and methods according to embodiments of the present invention.

FIG. 15 shows a block diagram of an example computer system 1500 usable with system and methods according to embodiments of the present invention.

Any of the computer systems mentioned herein may utilize any suitable number of subsystems. Examples of such subsystems are shown in FIG. 15 in computer apparatus 1500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 15 are interconnected via a system bus 1575. Additional subsystems such as a printer 1574, keyboard 1578, fixed disk 1579, monitor 1576, which is coupled to display adapter 1582, and others are shown. Peripherals and input/output (I/O) devices, which couple to I/O controller 1571, can be connected to the computer system by any number of means known in the art, such as serial port 1577. For example, serial port 1577 or external interface 1581 can be used to connect computer system 1500 to a wide area network such as the Internet, a mouse input device, or a scanner. The interconnection via system bus 1575 allows the central processor 1573 to communicate with each subsystem and to control the execution of instructions from system memory 1572 or the fixed disk 1579, as well as the exchange of information between subsystems. The system memory 1572 and/or the fixed disk 1579may embody a computer readable medium. Any of the values mentioned herein can be output from one component to another component and can be output to the user.

A computer system can include a plurality of the same components or subsystems, e.g., connected together by external interface 1581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

References include:

Lu P, Nakorchevskiy A, Marcotte E M: Expression deconvolution: a reinterpretation of DNA microarray data reveals dynamic changes in cell populations. Proc Natl Acad Sci USA 2003, 100:10370-10375;

Shen-Orr S S, Tibshirani R, Khatri P, Bodian D L, Staedtler F, Perry N M, et al. Cell type-specific gene expression differences in complex tissues. Nat. Methods. 2010 April; 7(4):287-9;

Zhao Y, Simon R. Gene expression deconvolution in clinical samples. Genome Med. 2010; 2(12):93;

U.S. Patent Publication US2006/0292572 by Robert O Stuart;

Foti, Maria, Paola Ricciardi-Castagnoli, and Francesca Granucci. 2007. "Gene expression profiling of dendritic cells by microarray." *Methods in Molecular Biology* (Clifton, N.J.) 380: 215-224;

Kobayashi, Scott D, Dan E Sturdevant, and Frank R DeLeo. 2007. "Genome-scale transcript analyses in human neutrophils." *Methods in Molecular Biology* (Clifton, N.J.) 412: 441-453;

Pike-Overzet, Karin, Dick de Ridder, Tom Schonewille, and Frank J T Staal. 2009. "DNA microarray studies of hematopoietic subpopulations." *Methods in Molecular Biology* (Clifton, N.J.) 506: 403-421. doi:10.1007/978-1-59745-409-4_27;

Fan, Hongtao, and Priti S Hegde. 2005. "The transcriptome in blood: challenges and solutions for robust expression profiling." *Current Molecular Medicine* 5 (1) (February): 3-10;

Mohr, Steve, and Choong-Chin Liew. 2007. "The peripheral-blood transcriptome: new insights into disease and risk assessment." *Trends in Molecular Medicine* 13 (10) (October): 422-432. doi:10.1016/j.molmed.2007.08.003;

Vartanian, Kristina, Rachel Slottke, Timothy Johnstone, Amanda Casale, Stephen R Planck, Dongseok Choi, Justine R Smith, James T Rosenbaum, and Christina A Harrington. 2009. "Gene expression profiling of whole blood: comparison of target preparation methods for accurate and reproducible microarray analysis." *BMC Genomics* 10: 2. doi: 10.1186/1471-2164-10-2;

Weber, Daniel Gilbert, Swaantje Casjens, Peter Rozynek, Martin Lehnert, Sandra Zilch-Schöneweis, Oleksandr Bryk, Dirk Taeger, et al. 2010. "Assessment of mRNA and microRNA Stabilization in Peripheral Human Blood for Multicenter Studies and Biobanks" *Biomarker Insights* 5: 95-102;

Chaussabel, Damien, Virginia Pascual, and Jacques Banchereau. 2010. "Assessing the human immune system through blood transcriptomics." *BMC Biology* 8: 84. doi: 10.1186/1741-7007-8-84;

Mesko, Bertalan, Szilard Poliska, and Laszlo Nagy. 2011. "Gene expression profiles in peripheral blood for the diagnosis of autoimmune diseases." *Trends in Molecular Medicine* 17 (4) (April): 223-233. doi:10.1016/j.molmed.2010.12.004;

Laudanski et al. "Cell-specific expression and pathway analyses reveal alterations in trauma-related human T cell and monocyte pathways." Proc. Natl. Acad. Sci. U.S.A. 2006 Oct. 17; 103(42):15564-9;

Whitney, et al 2003. "Individuality and Variation in Gene Expression Patterns in Human Blood." Proceedings of the National Academy of Sciences of the United States of America 100 (4) (February 18): 1896-1901;

Palmer, et al. 2006. "Cell-type Specific Gene Expression Profiles of Leukocytes in Human Peripheral Blood." BMC Genomics 7: 115;

Watkins, et al 2009. "A HaemAtlas: Characterizing Gene Expression in Differentiated Human Blood Cells." Blood 113 (19) (May 7): e1-9;

Bryant, et al. 2009. "Detection of Gene Expression in an Individual Cell Type Within a Cell Mixture Using Microarray Analysis." PloS One 4 (2): e4427;

Butt and Swaminathan, Biomarkers, February/2011;

U.S. Patent Publications 2007/0037144, US2007/0020618, US20110070581; and

U.S. Pat. Nos. 7,598,031; 6,365,352, and 7,888,030, all of which are incorporated for all purposes.

All patents, patent applications, publications, and descriptions mentioned above are herein incorporated by reference in their entirety for all purposes. None is admitted to be prior art.

What is claimed is:

1. A method for measuring a genomic expression in a first subpopulation of cells of a sample of a cell mixture, the method comprising:
    identifying a plurality of subpopulation informative genes including:
        at least one subpopulation target gene; and
        at least one subpopulation reference gene having a lower biological variation relative to the subpopulation target gene, each of the plurality of subpopulation informative genes identified as having at least a predetermined percentage of its transcripts in one or more calibration samples of the cell mixture contributed by the cells of the first subpopulation, the cell mixture containing a plurality of different subpopulations of cells, the predetermined percentage being equal to or greater than 50%;
    performing one or more reactions involving the cell mixture sample;
    measuring signals corresponding to the plurality of subpopulation informative genes from the one or more reactions involving the cell mixture sample, wherein the signals are proportional to amounts of transcripts of the plurality of subpopulation informative genes in the cell mixture sample;
    receiving, at a computer system, the signals obtained from the measurement of the cell mixture sample;
    using the signals to determine, with the computer system, a first amount of transcripts of the at least one subpopulation target gene in the cell mixture sample and a second amount of transcripts of the at least one subpopulation reference gene in the cell mixture sample; and
    calculating a parameter that is a relative value of the first amount to the second amount, the parameter providing a measurement of an amount of genomic expression of the subpopulation target gene in the first subpopulation of cells of the cell mixture sample.

2. The method of claim 1, wherein the one or more reactions involve polymerase chain reaction (PCR), microarray, or sequencing.

3. The method of claim 1, further comprising:
    comparing the parameter to one or more cutoff values to determine a classification of the cell mixture sample.

4. The method of claim 3, wherein the classifications include whether the cell mixture sample is in a diseased state or a non-diseased state.

5. The method of claim 4, wherein a range of values are associated with the non-diseased state.

6. The method of claim 1, wherein identifying the plurality of subpopulation informative genes for the first subpopulation includes:
    receiving data regarding expression of a plurality of genes in the first subpopulation of cells and regarding expression of the plurality of genes in one or more calibration cell mixtures corresponding to the one or more calibration samples;
    identifying a first set of genes that are expressed in the first subpopulation of cells based on the data;
    receiving a proportional cell count of the first subpopulations of cells in the one or more calibration cell mixtures; and
    analyzing the data to determine:
        a first expression level for each of the first set of genes in the one or more calibration cell mixtures; and
        a respective expression level for each of the first set of genes in the first subpopulation; and
    for each of the genes in the first set:
        using the proportional cell count and the respective expression level to determine whether the first subpopulation contributes at least the predetermined percentage of transcripts of the respective gene in the one or more calibration cell mixtures relative to the first expression level.

7. The method of claim 1, wherein identifying the plurality of subpopulation informative genes for the first subpopulation includes:
    receiving data regarding which of a plurality of genes are expressed in different subpopulations of cells in one or more calibration cell mixtures corresponding to the one or more calibration samples;
    receiving a respective proportional cell count of each of the different subpopulations in the one or more calibration cell mixtures, the respective proportional cell counts including a first proportional cell count P(1) for the first subpopulation;
    identifying a first set of genes that are expressed in the first subpopulation of cells based on the data;
    for each of the genes in the first set:
    analyzing the data to determine a respective expression level for the respective gene in each of the different subpopulations in which the respective gene is expressed, the respective expression level including a first expression level Ep(1) for the first subpopulation;
    using the equation $$EP(1)*P(1) \geq \frac{C\ \%}{(1-C\ \%)}\sum_{i=2}^{N} Ep(i)*P(i)$$

to determine whether the first subpopulation contributes at least the predetermined percentage of transcripts of the respective gene in the one or more calibration cell mixtures, where N is an integer corresponding to a number of subpopulation in which the respective gene is expressed, and C % is the predetermined percentage.

8. The method of claim 1, wherein the first subpopulation is selected from a group consisting of neutrophils, lymphocytes, monocytes, eosinophils, basophils, natural killer cells, CD3 total T cells, CD4 T cells, CD8 T cells, and , B cell lymphocytes.

9. The method of claim 1, wherein the predetermined percentage is 66% or 75%.

10. The method of claim 1, wherein the first subpopulation is B lymphocytes and the cell mixture sample is a blood sample, wherein the at least one subpopulation reference gene includes at least one selected from: TNFRSF13 C, KLHL14, and FREB.

11. The method of claim 1, wherein the first subpopulation is T lymphocytes and the cell mixture sample is a blood sample, wherein the at least one subpopulation reference gene includes GIMAP7 and/or LRRN3.

12. The method of claim 1, wherein the first subpopulation is granulocytes and the cell mixture sample is a blood sample, wherein the at least one subpopulation reference gene includes AQP1 and/or SOD2.

13. The method of claim 1, wherein identifying a subpopulation reference gene for the first subpopulation includes
receiving, at a computer, data regarding which of a plurality of genes are expressed in the first subpopulation of cells in a plurality of cell-mixture samples corresponding to the calibration samples, each cell-mixture sample containing a plurality of different subpopulations of cells;
identifying, by the computer, a first set of genes that are expressed in the first subpopulation of cells based on the data;
analyzing, with the computer, the data to determine a respective expression level for each of the first set of genes in each of a plurality of first subpopulation samples, each first subpopulation sample being from a different cell-mixture sample of a different subject;
identifying a subset of subpopulation genes that each have at least a predetermined percentage of their respective transcripts in the plurality of cell-mixture samples contributed by the cells of the first subpopulation, the predetermined percentage being equal to or greater than 50%, wherein the identifying uses the respective expression levels; and
analyzing respective expression levels of the subset of subpopulation genes to identify at least one subpopulation reference gene that has a variance of expression levels among the first subpopulation samples of less than a threshold.

14. The method of claim 13, further comprising:
determining a coefficient of variance of the gene expression level as the variance of expression level, wherein threshold is predetermined and is one hundred percent.

15. The method of claim 13, further comprising:
determining a coefficient of variance of the gene expression level as the variance of expression level, wherein threshold is predetermined and in the range of 20% to 200%.

16. The method of claim 13, wherein the subpopulation reference gene has the lowest variance of expression levels among the subset of subpopulation genes.

17. The method of claim 13, wherein identifying the subset of subpopulation genes includes using expression levels of the subpopulation genes that are measured relative to expression levels of a housekeeping gene that has uniform expression over multiple subpopulations.

18. The method of claim 13, wherein identifying the subset of subpopulation genes for the first subpopulation includes:
receiving a proportional cell count of the first subpopulations of cells in the plurality of cell-mixture samples;
analyzing the data to determine a first expression level for each the first set of genes in the cell-mixture samples;
for each of the genes in the first set:
using the proportional cell count and the respective expression level to determine whether the first subpopulation contributes at least the predetermined percentage of transcripts of the respective gene in the cell-mixture samples relative to the first expression level.

19. The method of claim 13, wherein identifying the subset of subpopulation genes for the first subpopulation includes:
receiving data regarding which of a plurality of genes are expressed in different subpopulations of cells in the plurality of cell-mixture samples;
receiving a respective proportional cell count of each of the different subpopulations of cells in the plurality of cell mixtures, the respective proportional cell counts including a first proportional cell count P(1) for the first subpopulation;
for each of the genes in the first set:
analyzing the data to determine a respective expression level for the respective gene in each of the different subpopulations in which the respective gene is expressed, the respective expression level including a first expression level Ep(1) for the first subpopulation;
using the equation $$EP(1) * P(1) \geq \frac{C\%}{(1-C\%)} \sum_{i=2}^{N} Ep(i) * P(i)$$

to determine whether the first subpopulation contributes at least the predetermined percentage of transcripts of the respective gene in the plurality of cell mixtures, where N is an integer corresponding to a number of subpopulation in which the respective gene is expressed, and C % is the predetermined percentage.

20. The method of claim 1, wherein the plurality of different subpopulations of cells includes at least three different subpopulations of cells.

21. The method of claim 13, wherein the plurality of different subpopulations of cells includes at least three different subpopulations of cells.

22. The method of claim 1, wherein the at least one subpopulation reference gene is selected from Table II and wherein the first subpopulation of cells is B lymphocytes.

23. The method of claim 1, wherein the at least one subpopulation reference gene is selected from Table III and wherein the first subpopulation of cells is CD4 T lymphocytes.

24. The method of claim 1, wherein the at least one subpopulation reference gene is selected from Table IV and wherein the first subpopulation of cells is CD8 T lymphocytes.

25. The method of claim 1, wherein the at least one subpopulation reference gene is selected from Table V and wherein the first subpopulation of cells is granulocytes.

26. The method of claim 1, wherein the at least one subpopulation reference gene is selected from Table VI and wherein the first subpopulation of cells is T lymphocytes.

* * * * *